US008865199B2

(12) United States Patent
Coleman et al.

(10) Patent No.: US 8,865,199 B2
(45) Date of Patent: Oct. 21, 2014

(54) BIOMATRIX COMPOSITION AND METHODS OF BIOMATRIX SEEDING

(75) Inventors: Michael E. Coleman, The Woodlands, TX (US); Eckhard U. Alt, Houston, TX (US); Ron Stubbers, Houston, TX (US)

(73) Assignees: Ingeneron, Inc., Houston, TX (US); Board of Regents of the University of Texas System, Austin, TX (US)

( * ) Notice: Subject to any disclaimer, the term of this patent is extended or adjusted under 35 U.S.C. 154(b) by 824 days.

(21) Appl. No.: 12/619,977

(22) Filed: Nov. 17, 2009

(65) Prior Publication Data

US 2010/0124563 A1 May 20, 2010

Related U.S. Application Data

(60) Provisional application No. 61/115,457, filed on Nov. 17, 2008.

(51) Int. Cl.
| | | |
|---|---|---|
| A61F 2/00 | (2006.01) | |
| A01N 63/00 | (2006.01) | |
| A01N 65/00 | (2009.01) | |
| C12M 1/00 | (2006.01) | |
| C12M 3/00 | (2006.01) | |
| A61L 27/38 | (2006.01) | |
| A61K 35/12 | (2006.01) | |

(52) U.S. Cl.
CPC .............. *A61L 27/3804* (2013.01); *A61K 35/33* (2013.01)
USPC ..... 424/423; 424/93.7; 435/283.1; 435/307.1

(58) Field of Classification Search
USPC ................... 424/423, 93.7; 435/283.1, 307.1
See application file for complete search history.

(56) References Cited

U.S. PATENT DOCUMENTS

| | | |
|---|---|---|
| 5,035,708 A | 7/1991 | Achas et al. |
| 5,079,160 A | 1/1992 | Lacy et al. |
| 5,372,945 A | 12/1994 | Achas et al. |
| 5,409,833 A | 4/1995 | Hu et al. |
| 5,486,359 A | 1/1996 | Caplan et al. |
| 5,756,291 A | 5/1998 | Griffin et al. |
| 5,786,207 A | 7/1998 | Katz et al. |
| 5,800,537 A | 9/1998 | Bell |
| 5,837,539 A | 11/1998 | Caplan et al. |
| 5,877,299 A | 3/1999 | Thomas et al. |
| 6,117,985 A | 9/2000 | Thomas et al. |
| 6,139,757 A | 10/2000 | Ohmura et al. |
| 6,153,432 A | 11/2000 | Halvorsen et al. |
| 6,306,575 B1 | 10/2001 | Thomas et al. |
| 6,316,247 B1 | 11/2001 | Katz et al. |
| 6,342,344 B1 | 1/2002 | Thomas et al. |
| 6,391,297 B1 | 5/2002 | Halvorsen |
| 6,429,013 B1 | 8/2002 | Halvorsen et al. |
| 6,482,926 B1 | 11/2002 | Thomas et al. |
| 6,491,918 B1 | 12/2002 | Thomas et al. |
| 6,805,860 B1 | 10/2004 | Alt |
| 6,867,289 B1 | 3/2005 | Gorenstein et al. |
| 7,160,553 B2 | 1/2007 | Gibbins et al. |
| 7,358,284 B2 | 4/2008 | Griffey et al. |
| 7,390,484 B2 | 6/2008 | Fraser et al. |
| 7,452,532 B2 | 11/2008 | Alt |
| 2002/0033367 A1 | 3/2002 | Prince et al. |
| 2005/0084961 A1 | 4/2005 | Hedrick et al. |
| 2005/0153442 A1* | 7/2005 | Katz et al. ...................... 435/366 |
| 2005/0239988 A1* | 10/2005 | Levy et al. ...................... 528/44 |
| 2006/0141623 A1 | 6/2006 | Smith et al. |
| 2010/0285588 A1 | 11/2010 | Stubbers et al. |

FOREIGN PATENT DOCUMENTS

WO   WO 2007/009036   *   1/2007

OTHER PUBLICATIONS

Gimble et al. (Cytotherapy, 2003, 5 (5), 362-369).*
Ohata et al. (Molecular Human Reporduction, 2001, 7 (7), 665-670).*
Cowan et al. (Nature Biotechnology, 2004, 22, 560-567).*
Chen et al. (Macromol Biosci. 2002, 2, 67-77).*
Astori et al. Journal of Translational Medicine, 2007, 5, 55.*
Gobin et al. Structural and Mechanical Characteristics of Silk Fibroin and Chitosan Blend Scaffolds for Tissue Regeneration, J. Biomed. Mat. Res. Part A, 2005, 74A (3), 465-473.*
Altman et al. "Dermal matrix as a carrier for in vivo delivery of human adipose-derived stem cells," *Biomaterials*, 2008, 29(10):1431-1442.
Bai et al. "Electrophysiological Properties of Human Adipose Tissue-Derived Stem Cells," *Am J Physiol Cell Physiol*, 2007, 293(5):C1539-50.
Boquest et al "Isolation and transcription profiling of purified uncultured human stromal stem cells: Alteration of gene expression after in vitro cell culture," *Mol. Biol Cell*, 2005 16(3):1131-1141.
Cowan et al., "Adipose-derived adult stromal cells heal critical-size mouse calvarial defects," *Nat Biotechnol*, 2004, 22(5):560e7.

(Continued)

*Primary Examiner* — Gina C Justice
*Assistant Examiner* — Genevieve S Alley
(74) *Attorney, Agent, or Firm* — Wong, Cabello, Lutsch, Rutherford & Brucculeri, LLP

(57) ABSTRACT

Apparatus and methods are described for generating autologous tissue grafts, the apparatus including a point of care SVF isolation unit that includes a tissue digestion chamber in fluid communication with a lipid separating chamber, whereby SVF cells are isolated without centrifugation; and a cell seeding chamber in fluid communication with the SVF isolation unit, said cell seeding chamber adapted to support a cell scaffold. Methods and materials for cell seeding, including through the provision of micro rough scaffold surfaces, are also provided.

24 Claims, 12 Drawing Sheets

(56) References Cited

OTHER PUBLICATIONS

Dominici et al., "Minimal criteria for defining multipotent mesenchymal stromal cells. The International Society for Cellular Therapy position statement," *Cytotherapy*, 2006, 8:315-317.

Erdag and Sheridan, "Fibroblasts improve performance of cultured composite skin substitutes on athymic mice," *Burns*, 2004, 30(4): 322e8.

Fuchs et al., "Diaphragmatic reconstruction with autologous tendon engineered from mesenchymal amniocytes," *J Pediatr Surg*, 2004, 39(6): 834-8.

Gimble and Guilak, "Adipose-derived adult stem cells: isolation, characterization, and differentiation potential," *Cytotherapy*, 2003, 5(5):362-369.

Gobin et al., "Repair and regeneration of the abdominal wall musculofascial defect using silk fibroin-chitosan blend," *Tissue Eng*, 2006, 12(12): 3383-3394.

Griffiths et al., "Survival of Apligraf in acute human wounds" *Tissue Eng*, 2004, 10(7-8):1180.

Hauner et al., "Promoting effect of glucocorticoids on the differentiation of human adipocyte precursor cells cultured in a chemically defined medium," *J. Clin. Invest.*, Nov. 1989, 84(5):1663-70.

Hewett et al., "Isolation and characterization of microvessel endothelial cells from human mammary adipose tissue," *In Vitro Cell. Dev. Biol.*, 1992, 29:325-331.

Hollenberg and Yost, "Regulation of DNA synthesis in fat cells and stromal elements from rat adipose tissue," J. Clin. Invest., 1968, 47: 2485-2498.

Kern et al., "Isolation and culture of microvascular endothelium from tissue," *J. Clin. Invest.*, 1983, 71: 1822-1829.

Khor and Lim, "Implantable applications of chitin and chitosan." *Biomaterials*, 2003, 24(13):2339-2349.

Kim et al., "Wound healing effect of adipose-derived stem cells: A critical role of secretory factors on human dermal fibroblasts." *J Dermatol Sci*, 2007, 48(1):15-24.

Kim et al. "Direct comparison of human mesenchymal stem cells derived from adipose tissues and bone marrow III mediating neovascularization in response to vascular ischemia,"*Cell Physiol Biochem*, 2007, 20(6): 867-876.

Prockop, "Stemness" does not explain the repair of many tissues by mesenchymal stem/multipotent stromal cells (MSCs), *Clin Pharmacol Ther.*, Sep. 2007, 82(3):241-3.

Rodbell, "Metabolism of isolated fat cells: Effects of hormones on glucose metabolism and lipolysis," *J. Biol. Chem*, 1964, 239: 375-380.

Van et al., "Cytological and enzymological characterization of adult human adipocyte precursors in culture," *J. Clin. Invest.*, 1976, 58: 699-704.

Wagner and Matthews, "The isolation and culture of capillary endothelium from epidymal fat," *Microvasc. Res.*, 1975, 10: 286-297.

Wu, et al. "Mesenchymal stem cells enhance wound healing through differentiation and angiogenesis" *Stem Cells*, 2007, 25(10): 2648-59.

Zhang et al. "Transduction of bone-marrow derived mesenchymal stem cells by using lentivirus vectors pseudotypes with modified RD114 envelope glycoprotains," *J. Viral.*, 2004, 78: 1219-29.

Zuk et al "Human Adipose Tissue is a Source of Multipotent Stem Cells," *Mol. Biol. Cell*, 2002, 13: 4279-95.

Authorized Officer, Ellen Moyse, International Bureau of WIPO, International Preliminary Report on Patentability and Written Opinion, mailed Jun. 17, 2010, 11 pages.

Authorized Officer, Lee W. Young, International Bureau of WIPO, International Search Report and Written Opinion, Jan. 19, 2009, mailed Feb. 23, 2009, 12 pages.

European Patent Office, Supplementary European Search Report, EP Application No. 08856235.0, mailed Oct. 14, 2011, 6 pages.

\* cited by examiner

Figure 2A

| Sample | anti-CD31 | anti-CD34 | anti-CD44 | anti-CD45 | anti-CD71 | anti-CD73 | anti-CD90 | anti-CD105 | anti-CD117 | anti-CD146 | anti-Sca-1 | anti-SSEA-4 |
|---|---|---|---|---|---|---|---|---|---|---|---|---|
| Adherent | 5.36 | 85.3 | 88.6 | 6.07 | 44.1 | 77.9 | 76.5 | 4.17 | 2.21 | 7.74 | 8.84 | 3.84 |
| Non-adherent | 15.7 | 72.8 | 62.3 | 36.4 | 40 | 12.3 | 23.4 | 2.3 | 0 | 3.9 | 1.4 | 3.7 |

Total Yield – 40.2 x 10⁶/100 g
Viability – 93 %
Percent Adherent – 81 %

Figure 2B

| Sample | anti-CD31 | anti-CD34 | anti-CD44 | anti-CD45 | anti-CD71 | anti-CD73 | anti-CD90 | anti-CD105 | anti-CD117 | anti-CD146 | anti-Sca-1 | anti-SSEA-4 |
|---|---|---|---|---|---|---|---|---|---|---|---|---|
| Adherent | 2.86 | 90.1 | 92.4 | 2.88 | 2.93 | 50.6 | 91.2 | 4.91 | 0.2 | 3.31 | 0.68 | 0.53 |
| Non-adherent | 34.65 | 61.2 | 38.8 | 41.9 | 17.8 | 13 | 50.7 | 1.95 | 0.78 | 16.55 | 0.19 | 21.65 |

Total Yield – 9.7 x 10⁶/100 g
Viability – 87 %
Percent Adherent – 76 %

Figure 3

| Sample | anti-CD31 | anti-CD34 | anti-CD44 | anti-CD45 | anti-CD71 | anti-CD73 | anti-CD90 | anti-CD105 | anti-CD117 | anti-CD146 | anti-Sca-1 | anti-SSEA-4 |
|---|---|---|---|---|---|---|---|---|---|---|---|---|
| Fresh | 40.1 | 45.9 | 46.3 | 20.3 | 16.5 | 32.6 | 41.3 | 0 | 0 | 26.1 | 0 | 8.3 |

Total Yield 118.4 x 10⁶/100 g

Figure 4

| Gender | Anatomic Location | Collected Tissue Wt. | Cell Yield (x10⁶) | Percent Viability Hemacytometer | Percent Viability Live/Dead | Doubling Time, Hr. | Percent CFU |
|---|---|---|---|---|---|---|---|
| F | Thigh | 135.14 | 28.5 | 86.9 | 86.3 | 41.9 | 8.1 |
| M | Abdomen | 114.64 | 10.8 | 81.6 | 65 | 56.8 | 9.3 |
| F | Abdomen | 141.16 | 20.4 | 85.4 | 99.6 | 75.7 | 9.9 |
| F | Thigh/Flank | 107.7 | 41.9 | 88 | 99.9 | ND | 15.4 |
| F | Chest/Flank | 163.17 | 39 | 83.9 | 98.3 | 111.3 | 14.1 |
| F | Abdomen/Pubic | 151.3 | 55.6 | 89.4 | 68.5 | 69.1 | 16.2 |
| M | Chest/Flank | 152 | 16.1 | 59 | 64 | 103.5 | 14 |
| F | Thigh | | 36.2 | 91.1 | 88.7 | ND | 6.6 |
| Mean | | 138 | 30 | 82 | 83 | 76 | 12 |
| SD | | 20 | 16 | 11 | 17 | 27 | 3 |

Patient demographics, cell yield and adherent cell growth characteristics. ND – not done.

Figure 5

| Sample | % | CD31 | CD34 | CD44 | CD45 | CD71 | CD73 | CD90 | CD105 | CD117 | CD146 | Sca-1 | SSEA4 |
|---|---|---|---|---|---|---|---|---|---|---|---|---|---|
| AD | 94 | 6.6 | 62.5 | 77.5 | 26.2 | 62.6 | 70.5 | 70.5 | 67.5 | 10.1 | 8.7 | 46.2 | 9.0 |
| NAD | 6 | 5.6 | 68.9 | 66.7 | 56.1 | 17.4 | 4.0 | 7.6 | 1.3 | 0.3 | 7.3 | 6.5 | 7.4 |
| Total | | 6.5 | 62.9 | 76.8 | 28.0 | 59.9 | 66.5 | 66.7 | 63.5 | 9.5 | 8.6 | 43.8 | 8.9 |
| AD | 76 | 3.5 | 72.1 | 78.6 | 4.2 | 34.9 | 63.8 | 76.9 | 24.1 | 0.2 | 5.4 | 0.0 | 1.7 |
| NAD | 24 | 20.0 | 26.7 | 54.7 | 55.7 | 6.7 | 6.4 | 22.2 | 1.8 | 0.2 | 10.9 | 0.0 | 11.8 |
| Total | | 7.4 | 61.2 | 72.8 | 16.5 | 28.1 | 50.0 | 63.7 | 18.7 | 0.2 | 6.7 | 0.0 | 4.1 |
| AD | 84 | 4.8 | 81.3 | 79.1 | 4.7 | 32.7 | 52.6 | 78.8 | 15.6 | 0.8 | 3.6 | 0.9 | 2.9 |
| NAD | 16 | 7.2 | 43.6 | 40.4 | 25.8 | 2.4 | 2.0 | 15.2 | 1.2 | 0.0 | 6.1 | 0.4 | 4.0 |
| Total | | 5.2 | 75.3 | 72.9 | 8.1 | 27.9 | 44.5 | 68.6 | 13.3 | 0.7 | 4.0 | 0.8 | 3.1 |
| AD | 86 | 8.2 | 64.2 | 67.8 | 13.7 | 45.4 | 53.9 | 60.4 | 52.9 | 8.9 | 6.4 | 29.5 | 8.9 |
| NAD | 14 | 11.6 | 26.2 | 60.5 | 49.3 | 33.4 | 6.6 | 16.1 | 5.3 | 3.7 | 12.6 | 5.2 | 8.3 |
| Total | | 8.7 | 58.9 | 66.8 | 18.7 | 43.7 | 47.3 | 54.2 | 46.2 | 8.2 | 7.3 | 26.1 | 8.8 |
| AD | 74 | 7.2 | 86.8 | 86.4 | 10.8 | 38.4 | 63.0 | 82.8 | 24.1 | 6.5 | 7.0 | 6.6 | 8.8 |
| NAD | 26 | 10.7 | 29.1 | 55.3 | 50.5 | 7.3 | 9.0 | 22.3 | 3.6 | 2.1 | 5.9 | 0.5 | 9.7 |
| Total | | 8.1 | 71.8 | 78.3 | 21.1 | 30.3 | 49.0 | 67.1 | 18.8 | 5.4 | 6.7 | 5.0 | 9.0 |
| AD | 83 | 3.8 | 60.0 | 51.7 | 35.7 | 31.6 | 46.4 | 61.1 | 10.2 | 0.2 | 3.7 | 1.1 | 5.1 |
| NAD | 17 | 9.7 | 18.5 | 44.8 | 47.3 | 9.2 | 8.4 | 17.2 | 0.0 | 0.0 | 6.2 | 0.0 | 5.0 |
| Total | | 4.8 | 52.9 | 50.5 | 37.7 | 27.8 | 39.9 | 53.6 | 8.5 | 0.2 | 4.1 | 0.9 | 5.1 |
| AD | 91 | 7.3 | 84.9 | 79.1 | 4.5 | 47.5 | 53.8 | 64.7 | 31.9 | 0.2 | 4.0 | 0.0 | 5.0 |
| NAD | 9 | 16.5 | 41.4 | 50.7 | 46.0 | 3.8 | 3.2 | 41.4 | 1.8 | 6.0 | 17.1 | 0.3 | 6.7 |
| Total | | 8.1 | 81.0 | 76.6 | 8.3 | 43.6 | 49.3 | 62.6 | 29.2 | 0.7 | 5.2 | 0.0 | 5.2 |
| AD | 88 | 0.4 | 68.7 | 68.9 | 14.7 | 17.2 | 53.5 | 66 | 39.1 | 0.8 | 63.9 | 11.9 | 1.2 |
| NAD | 12 | 7.7 | 10.6 | 60.8 | 58.2 | 9.5 | 9.6 | 19.3 | 4.6 | 14 | 53.5 | 27.7 | 13.6 |
| Total | | 1.3 | 61.7 | 67.9 | 19.9 | 16.3 | 48.2 | 60.4 | 35.0 | 2.4 | 62.7 | 13.8 | 2.7 |
| Total Mean | | 6.3 | 65.7 | 70.3 | 19.8 | 34.7 | 49.3 | 62.1 | 29.1 | 3.4 | 13.2 | 11.3 | 5.9 |
| SD | | 2.5 | 9.4 | 9.0 | 9.8 | 13.6 | 7.7 | 5.7 | 18.5 | 3.8 | 20.1 | 16.0 | 2.7 |

AD – Adherent cells. NAD – Non-adherent cells.

BIOMATRIX COMPOSITION AND METHODS OF BIOMATRIX SEEDING

CROSS REFERENCE TO RELATED APPLICATIONS

This application claims priority to U.S. Provisional Application Ser. No. 61/115,457 filed Nov. 17, 2008, which is incorporated herein by reference.

FIELD OF THE INVENTION

This invention relates generally to apparatus, compositions and methods for the generation of implantable matrices seeded with reparative cell populations.

BACKGROUND OF THE INVENTION

The present invention relates generally to tissue scaffolds seeded with reparative cell populations for tissue repair, including myocardial repair. Without limiting the scope of the invention, its background is described in connection with existing methods and compositions of implantable materials for treating physical defects and wound healing.

Roughly 1% of humans are born with an atrial septal defect (ASD) which permits a shunt between the right and left atrium. Other deficiencies include ventricular septum defects and patent foramen ovale (PFO). Each of these defects are amenable to treatment by occlusion either by direct surgical techniques in suturing a patch or by placement of an occluder non-invasively. Current occluders and patch materials include non-absorbable but biocompatible materials such as polytetrafluroethylene (PTFE or Teflon® patches such as the GORE HELEX® Septal Occluder), woven polyester (Dacron® fabric disk devices such as CardioSEAL® and STAR-Flex®), stainless steel and polyurethane (i.e. the Sideris buttoned devices), nickel titanium shape memory alloys (i.e. the Amplatzer septal occluder constructed of a mesh of Nitinol wires) or cobalt-chromium-nickel alloys (Elgiloy). Although the synthetic patches are not absorbed, they act as a scaffold onto which normal tissue can grow and cover the defect, which is essentially "scarred" into place after about 3-6 months depending on the conditions of the defect.

For wound healing and reconstructive surgery, existing materials include the use of synthetic materials as well as biomaterials generated from human and other animal tissues, such as for example the acellular dermal matrices (ADM) derived from normal human skin (i.e. Alloderm® ADMs, also detailed in U.S. Pat. No. 7,358,284). Synthesized biodegradable scaffolds for tissue repair have been introduced for potential applications including tissue formation, expansion of host bone cells, cell transplantation, and bioactive molecule delivery. Preformed biodegradable scaffolds composed of polyglycolic acid (PGA) and poly L-lactic acid (PLLA) have been FDA-approved (i.e. Vicryl® polyglactin woven mesh). The biodegradable graft material, Dermagraft®, which has been approved for treatment of diabetic foot ulcers, is manufactured by seeding a polyglactin mesh with human fibroblasts which proliferate and coat the mesh with dermal collagen, matrix proteins, and growth factors before the mesh is cryopreserved.

The field of regenerative medicine has been extensively studying the potential of cell therapy for repair of injured or diseased tissue. To date, cells from multiple sources including embryonic stem cells, bone marrow derived mesenchymal stem cells, peripheral blood derived endothelial progenitor cells and mesenchymal stem cells, and selected adipose derived cells have been demonstrated to enhance tissue repair in one or more experimental models. Translation of these preclinical findings into a practical therapy is the subject of significant research. Since these research efforts are largely based on the premise that a single cell type, for example a pluripotent or totipotent stem cell, is the best choice for cell therapy, significant effort has been focused on identifying and then obtaining the target cell type.

It has been suggested that the post-graft mechanical behavior of ADM could be enhanced by cell seeding prior to implantation. (Erdag G, Sheridan R L. "Fibroblasts improve performance of cultured composite skin substitutes on athymic mice." *Burns* 30(4) (2004) 322e8; Fuchs J R, et al. "Diaphragmatic reconstruction with autologous tendon engineered from mesenchymal amniocytes" *J Pediatr Surg* 39(6) (2004) 834-8). Tissue engineering involving the delivery of autologous stem cells and progenitor cells seeded on scaffolds is currently at the animal discovery stage and involves the seeding of scaffolds followed by in vitro culture to produce relatively large pieces of tissue prior to implantation. Such pre-seeded and cultured scaffolds have been shown to be of value for tissue repair in animal models.

Recent research in the inventor's laboratories has proven that a mixture of early mesenchymal, multi-potent, lineage committed and lineage uncommitted stem/progenitor cells and fully differentiated cells can be obtained from many body tissue areas. The early mesenchymal uncommitted cells originate from the microvessels within the tissues. For practical reasons, adipose tissue is a source that is available in most animal and human species without disrupting the physiological functions of the body. It has been reported that adipose derived stromal cells seeded onto carrier bioprosthetics facilitated formation of new bone in an animal model. (Cowan C M, et al. "Adipose-derived adult stromal cells heal critical-size mouse calvarial defects" *Nat Biotechnol* 22(5) (2004) 560e7).

Typically, cells for matrix or scaffold seeding are isolated from donor tissue and cultured for an extended period of time. For example, the FDA approved Apligraf® skin grafts available from Organogenesis (Canton, Mass.) are manufactured by first forming a bovine collagen matrix which is plated with cultured human dermal fibroblasts isolated from human donor skin. Certain aspects of the manufacturing process are disclosed in Bell, U.S. Pat. No. 5,800,537. The donor fibroblasts are cultured on the collagen matrix for 6 days to form a dermal matrix. Next the dermal matrix is plated with cultured human keratinocytes to promote development of a stratum corneum layer. The entire process takes from 20 to 27 days prior to packaging. While useful, such a process does not utilize pluripotent cells and is clearly not amendable to a point of care process employing the patient's own (autologous) cells. Additionally, recent findings suggest that the cells do not survive long term and engraft in the recipient patient thus limiting the utility of this allogenic cell product (Griffiths M, et al, "Survival of Apligraf in acute human wounds" *Tissue Eng* 10(7-8) (2004) 1180).

Alternatively, in research applications, bone marrow aspirate cells have been obtained from patients and the cells have been held in place or physically "trapped" on the matrix by an artificial means such as by a thrombin induced clot for holding bone marrow aspirate onto an osteogenic matrix. While these methods may have some utility, they require a prolonged treatment program including several surgical interventions.

Methods and compositions for the generation of point-of-care cell seeded matrices have not been heretofore available and there continues to be an unmet need for implantable cell seeded matrices that maybe generated in a single procedure. Also needed are methods and apparatus that permit the isolation of reparative cell populations that are suitable for direct seeding on to biocompatible matrices.

The present invention provides methods and materials for the focal application of reparative cell populations, for example for repair of damaged neurons, muscle, tendons, joints and bone structures, repair of parenchymal organs such as liver, kidney, heart, or brain, and for repair of skin tissues including in the treatment of burns, hernias, and non-healing wounds. Methods and materials are provided to retain desirable cell populations on biocompatible scaffolds and to most effectively use the scaffold in conjunction with a fresh cellular preparation, which avoids a need to culture the cells.

BRIEF SUMMARY OF THE INVENTION

The invention described provides novel methods and apparatus for point-of-care isolation of reparative cell populations that does not rely on a cell property of being strongly adherent, as well as biocompatible matrices that are suitable for loading with the reparative cell populations and implanted without the need for prolonged culturing of the cells or without the need for preselecting cells by plastic adherence.

In one embodiment of the invention, a graft is provided that includes a biomaterial that is resorbable and is seeded with reparative cell population that allows a natural healing including by differentiation of cells from the population into different lineages depending on pretreatment of the cells and/or placement of the seeded biomaterial in specialized tissues that influence the differentiation pathway. For one non-limiting example, when implanted into the heart, certain of the pluripotent stem cells in the population may turn into fibroblasts while others may differentiate into specialized cells such as cardiomyocytes and endothelial cells, thus enabling an accelerated healing and remodeling process that most closely resembles a natural process.

In one embodiment, a method of generating tissue grafts is provided including the steps of: isolating stromal vascular fraction (SVF) cells from adipose tissue of a mammal, said SVF cells isolated by enzymatically digesting adipose tissue and separating out lipid containing cells by floatation, followed by collecting the SVF cells without centrifugation; applying the SVF cells to a first scaffold; incubating the SVF cells with the scaffold for less than 2 hours; and removing unbound SVF cells from the scaffold, thereby generating a cell seeded tissue graft. In one such embodiment, the cell seeded tissue graft is generated at a point-of-care and is implanted into the mammal without culturing the tissue graft whereas in alternative embodiments, the cell seeded tissue graft is cultured to expand populations of cells seeded on the graft prior to implanting into the mammal. In one embodiment of the aforementioned seeding step, the SVF cells are pushed into contact with the scaffold by pressure or by a partial vacuum. The methods and apparatus of the present invention are particularly useful in providing autologous tissue grafts.

If desired, a series of seeding steps may be employed wherein the unbound cells from a first seeding step are applied to second scaffold, wherein the second scaffold is adapted for binding of a different population of cells than the first scaffold, thereby generating at least two tissue grafts, each seeded with a different subpopulation of cells. By different subpopulations it is meant populations that exhibited different affinity for the two substrates at the time they were applied although it is understood that the different subpopulations may both contain at least some cells having similar or identical phenotypic markers.

In certain embodiments, the SVF cells are incubated with inductive media before, during or after being applied to the scaffold. For example, the inductive media may be adapted for generation of one or more of adipocytes, chondrocytes, endothelial cells, hepatocytes, myoblasts, neurons, and osteoblasts.

Preferably, the scaffolds to be seeded are comprised of a biocompatible or a biodegradable material. Suitable biocompatible materials include but are not limited to polytetrafluoroethylene, woven polyester, spun silicone, open foam silicone encased in microporous expanded PTFE, stainless steel, polypropylene, polyurethane, polycarbonate, nickel titanium shape memory alloys and cobalt-chromium-nickel alloys, and combinations thereof. Suitable biodegradable materials include but are not limited to silk fibroin-chitosan, acellular dermal matrices, collagen, polyglactin, and hyaluronic acid.

In certain embodiments, a cell attachment surface of the scaffold material is characterized by surface irregularities at a periodicity of 1-100 µm. In other embodiments, the surface feature micro surface irregularities at a periodicity of 5-20 µm. The surface irregularities may be created by treatment of at least one cell attachment surface of the scaffold by one or more of mechanical processes including by embossing, blasting, plasma etching, by controlling polymerization or drying processes, by heat application, by chemical etching, and by coating or printing. In one embodiment, at least one surface of the scaffold is characterized by a spongy texture formed by subjecting the nascent scaffold material to a partial vacuum during polymerization or drying.

The cell seeded tissue grafts disclosed herein may be utilized to treat one or more of: wound healing, burns, bone fractures, cosmetic defects, cartilage damage, tendon damage, ulcers, fistulas, hernias, retinal degeneration, treatment of ischemic disease, nerve injury, aneurysms, bladder wall repair, intestinal injury, and repair and reconstruction of vessels.

In one embodiment of the invention, one or more adherence agents selected to promote adherence of desired cell types to the scaffold are introduced into the seeding chamber before or during cell seeding. For example, the adherence agent may be selected from autologous plasma or serum and components thereof, cold insoluble globulin, carboxymethyl dextran, iron dextran, and hyaluronic acid and polymers thereof.

Also provided herein are apparatus for generating tissue grafts, said apparatus including a point of care SVF isolation unit that includes a tissue digestion chamber in fluid communication with a lipid separating chamber, whereby SVF cells are isolated without centrifugation; and a cell seeding chamber in fluid communication with the SVF isolation unit, said cell seeding chamber adapted to support a cell scaffold. In one embodiment, the cell seeding chamber is a dedicated chamber having an upper portion and a lower portion separated by a support member for the scaffold and further comprising at least one inlet port on the upper portion and at least one exit port on the lower portion. The exit port may in some embodiments be adapted for attachment to a vacuum or a pump whereby the SVF cells can be pulled from the upper portion to the lower portion across the scaffold. In some embodiments, the cell seeding chamber further includes a drain port in the upper portion. In other embodiments a plurality of seeding chambers are provided, linked in seriatim through a fluid conduit.

In one embodiment of the invention, a tissue graft is provided that includes a freshly isolated reparative cell preparation seeded onto a biomaterial, wherein the reparative cell preparation is seeded onto the biomaterial in an integrated apparatus that is employed to first isolate the reparative cell preparation and then seed the reparative cell preparation onto the biomaterial.

In one method of the invention, a method of generating a cell-seeded, biocompatible matrix at the point of care is provided including: isolating a population of cells at the point of care, said cells including multi-potent progenitor cells, endothelial cells, and fibroblasts; conveying the isolated population of cells onto a biocompatible matrix in a seeding chamber; allowing the cells to adhere to the biocompatible matrix at the point of care; and removing cells that are unbound to the matrix, thereby generating a cell-seeded, biocompatible matrix suitable for implantation into a patient at the point of care. By point of care it is meant at or near to the site of patient care, such as for example, in or near the operating suite or bedside. In an example of a point of care procedure, donor tissue is harvested from a patient, desired cell populations isolated, and a tissue graft prepared and implanted into the patient, all such steps occurring at or near to the site of patient care and at one clinic or hospital visit. In one embodiment of the method, a cell-seeded, biocompatible matrix is provided in less than about 4 hours in an integrated process at the point of care, wherein the process includes isolation of a heterogeneous reparative cell population and immediately seeding the heterogeneous reparative cell population onto the biocompatible matrix for implantation.

In one embodiment of the invention, a method of producing a cell-seeded, biocompatible matrix at the point of care is provided that includes: providing a biocompatible matrix that is modified to promote cell adherence; seeding the biocompatible matrix with a freshly isolated heterogeneous reparative cell population that contains cells having a plastic-adherent property as well as cells that lack a property of plastic adherence; forcing the freshly isolated heterogeneous reparative cell population into contact with the biocompatible matrix by applied pressure, vacuum or electric field. The biocompatible matrix may be optionally modified to promote cell adherence via chemical or physical modification of the matrix, or coating of the matrix with a biodegradable coating. For example, the modification may include treatment of at least one cell attachment surface of the scaffold by one or more of embossing, blasting, plasma etching, by controlling polymerization processes, by heat application, by chemical etching, and by coating or printing. Alternatively, or in addition, the modification may include coating with an adherence agent selected from the group consisting of: autologous plasma or serum and components thereof, cold insoluble globulin, carboxymethyl dextran, iron dextran, and hyaluronic acid and polymers thereof.

BRIEF DESCRIPTION OF THE DRAWINGS

For a more complete understanding of the present invention, including features and advantages, reference is now made to the detailed description of the invention along with the accompanying figures:

FIGS. 2A and B represent characterization data for reparative cell populations isolated according to the process depicted in FIG. 1.

FIG. 3 represents characterization data for freshly isolated reparative cell populations that have not been separated into adherent and non-adherent populations.

FIGS. 4 and 5 represent characterization data for freshly isolated reparative cell populations.

In FIG. 8 a series of selective seeding chambers are utilized in serial fashion for positive or negative selection or a combination thereof.

DETAILED DESCRIPTION OF THE INVENTION

Figure 1:
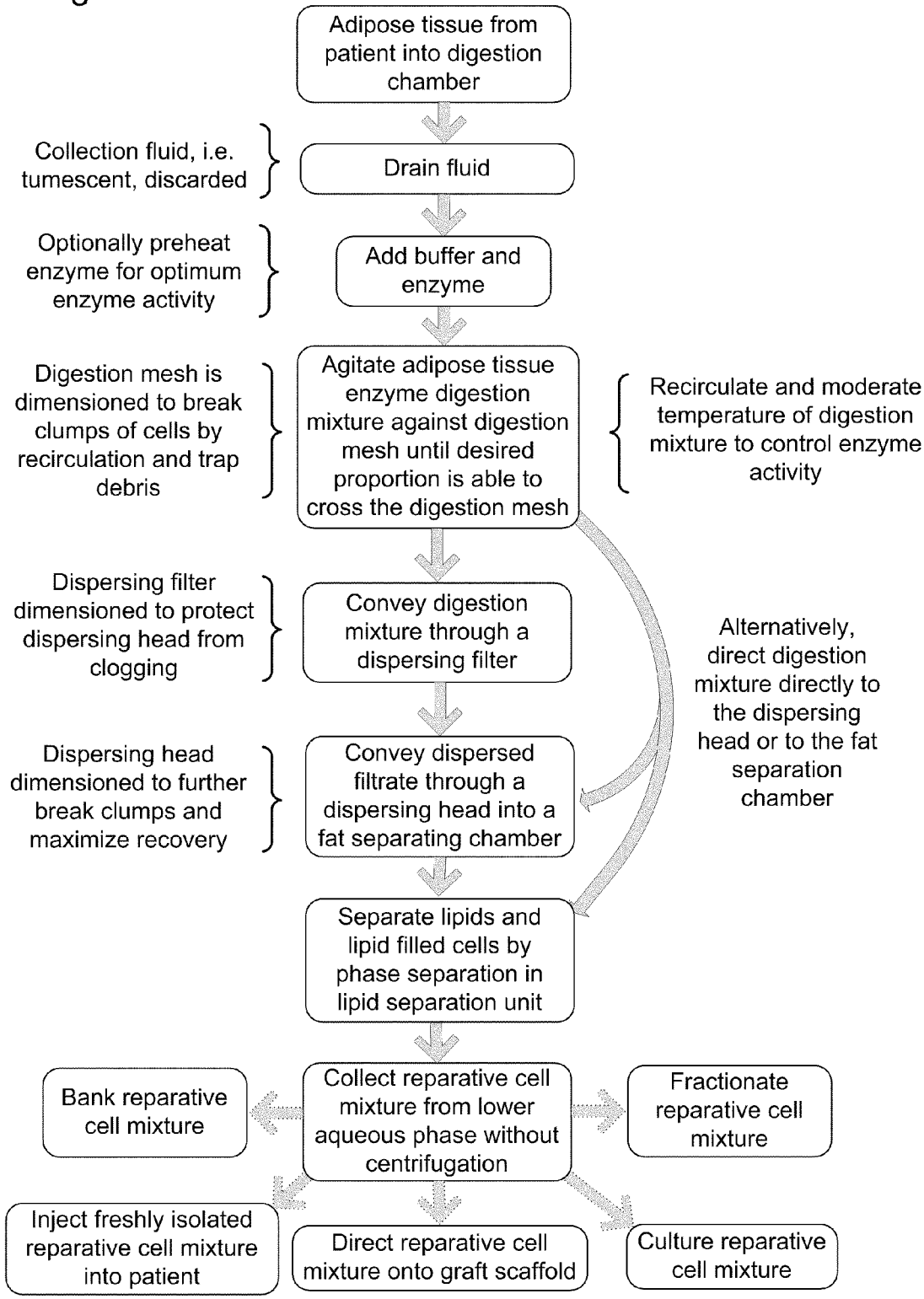
FIG. 1 is a flow chart of a reparative cell isolation method according to one embodiment of the present invention.

While the making and using of various embodiments of the present invention are discussed in detail below, it should be appreciated that the present invention provides many applicable inventive concepts that can be employed in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Increasing evidence suggests that stem cells are residents of a micro-vascular niche, on stand-by for tissue repair as needed. However, with extensive tissue damage, the local pool of stem cells available for repair is considered insufficient to fully correct the deficiency. Discarded adipose tissue obtained from liposuction procedures contains a significant number of mesenchymal stem cells accessed via a relatively low-risk surgical intervention. Adipose tissue is highly vascularized and is thus a source of endothelial cells, smooth muscle cells, its progenitors and of early multipotent mesenchymal stem cells.

Adipose tissue is characterized by the presence of mature adipocytes bound in a connective tissue framework termed the "stroma." In the present invention, stromal cells generally refers to cells resident in the connective tissue of an organ or tissue. Non-limiting examples of such cells include fibroblasts, macrophages, monocytes, pericytes, endothelial cells, inflammatory cells, progenitors and early undifferentiated mesenchymal stem cells. Such cells also participate in tissue maintenance and repair, typically as supportive cells. The stroma of adipose tissue includes an array of cells that do not include the lipid inclusions that characterize adipocytes. These include preadiopcytes, fibroblasts, vascular smooth muscle cells, endothelial cells, monocyte/macrophages and lymphocytes.

When the connective tissue of adipose tissue is digested, such as with collagenase, the lipid containing adipocytes can be separated from the other cell types. In 1964, Rodbell reported the use of collagenase to dissociate adipose tissue into a cellular suspension that could then be fractionated by centrifugation into an upper, lipid-filled adipocyte fraction, and a cell pellet comprised of non lipid-filled cells. The pelleted non-adipocyte fraction of cells isolated from adipose tissue by enzyme digestion has been termed the "stromal vascular cell" or SVF population. (Rodbell M. "Metabolism of isolated fat cells: Effects of hormones on glucose metabolism and lipolysis" *J. Biol. Chem.* 239 (1964) 375-380).

Heretofore, adipocytes have been separated from the SVF by centrifugation wherein the adipocytes float and the cells of the SVF pellet. Typically however, the SVF is subject to further processing and selection, including plastic adherence. Cells from the stromal vascular fraction that have been subject to plastic adherence are typically referred to as cultured stromal vascular cells or "adipose tissue-derived stromal cells" (ADSC). Not withstanding other definitions that may exist in the art, as used herein, the term "stromal vascular fraction cells" refers to all of the constituent cells of adipose tissue after enzyme digestion and removal of adipocytes and are not limited to plastic adherent cells.

Researchers have studied the makeup of the stromal vascular fraction of adipose tissue across a range of disciplines. Typically, the stromal vascular fraction cells that are adherent have comprised the population that has been studied in culture. In addition to fibroblasts, the stromal vascular fraction of adipose tissue has been shown to contain, among other cell types, microvessel endothelial cells, vascular progenitor cells, adipocyte progenitor cells (preadipocytes), and multipotent progenitor cells. Subsequent to Rodbell's original isolation, others, using in vitro and in vivo models, identified cells within the SVF that could differentiate into adipocytes. These cells were termed preadipocytes and were identified as plastic adherent cells within the SVF. (Hollenberg C H and Vost A. "Regulation of DNA synthesis in fat cells and stromal elements from rat adipose tissue" *J. Clin. Invest.* 47 (1968) 2485-2498; Van R L R, Bayliss C E, and Roncari D A K "Cytological and enzymological characterization of adult human adipocyte precursors in culture" *J. Clin. Invest.* 58 (1976) 699-704.

Using the basic methodology of Rodbell, but capturing endothelial cell clusters on a 30 μm filter versus collection of the entire stromal vascular pellet, it was demonstrated beginning in the 1970's that microvascular endothelial cells could be prepared from human adipose tissue. (Wagner R C and Matthews M A. "The isolation and culture of capillary endothelium from epidymal fat" *Microvasc. Res.* 10 (1975) 286-297). Interestingly, the so described "microvascular endothelial cells" from adipose tissue, unlike microvascular endothelial cells from other tissues, were observed to be adherent to plastic and as such could be easily cultured. See e.g. Kern P A, Knedler A, and Eckel R H. "Isolation and culture of microvascular endothelium from adipose tissue" *J. Clin. Invest.* 71 (1983) 1822-1829; Hewett P W, et al "Isolation and characterization of microvessel endothelial cells from human mammary adipose tissue" *In Vitro Cell. Dev. Biol.* 29 (1992) 325-331.

Caplan and Haynesworth (Osiris U.S. Pat. No. 5,486,359) described isolation of pluripotent mesenchymal stem cells from bone marrow using Percoll gradient separation and plating of the lowest density fraction on plastic. The isolated mesenchymal stem cells were plastic adherent and had fibroblast-like morphology. A panel of monoclonal antibodies was developed to these cells and including antibodies termed SH2, SH3 and SH4. These antibodies now have the following correlated CD markers: SH2 (CD105), SH3 and SH4 (CD73). Davis-Sproul et al. (Osiris U.S. Pat. No. 6,387,367) described isolation of pluripotent mesenchymal stem cells from bone marrow or blood using density gradient separation and collection of the light density cells followed by immunomagnetic bead separation of CD45+ cells. These cells were also positive for SH3 (a.k.a. CD 73) or SH2 (a.k.a. CD 105) and could be pre-selected for these markers.

Yuan-di Halvorsen (Artecel U.S. Pat. No. 6,391,297) used the SVC isolation technique of Rodbell, to wit, collagenase digestion and centrifugation, followed by plastic adherence to isolate stromal cells from adipose tissue. The stromal cells were cultured and induced to differentiate into either adipocytes by the bone marrow stem cell differentiation method of Hauner, which involved culture in a serum free medium supplemented with triiodothyronine, insulin and glucocorticoid (*J. Clin. Invest.* 84 (1989) 1663), or into osteoblasts using osteoplast differentiation medium which critically included β-glycerophosphate and ascorbate-2-phosphate. Later, Yuan-di Halvorsen described that stromal cells isolated from adipose tissue by collagenase digestion and centrifugation followed by plastic adherence could be induced to differentiate into preadipocytes by culture in a medium that critically included thiazolidinedione followed by culture in a medium critically including glucose, insulin and glucocorticoid. (ZenBio, U.S. Pat. No. 6,153,432, filed Jan. 29, 1999). Yuan-di Halvorsen et al (Artecel U.S. Pat. No. 6,429,013) later used the stromal vascular cell isolation technique of the above referenced U.S. Pat. No. 6,153,432, to isolate adipose-derived stromal cells that were induced to differentiate into chondrocytes by culture with a differentiation medium that included a glucocorticoid such as dexamethasone and a member of the TGF-β superfamily.

The ability of plastic adherent SVF cells to differentiate into multiple lineages fit the criteria of multipotent mesenchymal stem cells. (See review by Zuk et al "Human Adipose Tissue is a Source of Multipotent Stem Cells" *Mol. Biol. Cell* 13 (2002) 4279-95). In 2005, the International Society for Cellular Therapy (ISCT) stated that the currently recommended term for plastic-adherent cells isolated from bone marrow and other tissues is multipotent mesenchymal stromal cells (MSC) in lieu of the prior "stem cell" term.

As used herein the term Mesenchymal Stromal Cell (MSC) means the definition adopted by the International Society for Cellular Therapy and published in a position paper by Dominici et al, *Cytotherapy* 8 (2006) 315. In accordance with the position paper, MSC must exhibit:

1) adherence to plastic in standard culture conditions using tissue culture flasks;
2) a specific surface antigen (Ag) phenotype as follows:
    positive (≥95% +) for CD105 (endoglin, formerly identified by MoAb SH2), CD73 (ecto 5'nucleotidase, formerly identified by binding of MoAbs SH3 and SH4), CD90 (Thy-1), and negative (≤2% +) for CD14 or CH11b (monocyte and macrophage marker), CD34 (primitive hematopoietic progenitor and endothelial cell marker), CD45 (pan-leukocyte marker), CD79α or CD19 (B cells), and HLA-DR (unless stimulated with IFN-γ); and 3) tri-lineage mesenchymal differentiation capacity: able to differentiate in vitro into osteoblasts, adipocytes and chondrocytes in inductive media.

MSC have been traditionally defined as spindle-shaped or fibroblast-like plastic adherent cells. Although originally isolated from bone marrow, MSC have now been isolated from a variety of tissues including bone periosteum, trabecular bone, adipose tissue, synovium, skeletal muscle, dental pulp and cord blood.

Adipose-derived stem cells (ADSCs) have been reported to confer benefits in vivo including as angiogenic agents and in promoting multi-lineage restoration of soft tissue defects. See Altman A M, et al. "Dermal matrix as a carrier for in vivo delivery of human adipose-derived stem cells." *Biomaterials* 29(10) (2008) 1431-1442; Kim W S et al. "Wound healing effect of adipose-derived stem cells: A critical role of secretory factors on human dermal fibroblasts." *J Dermatol Sci* 48(1) (2007) 15-24; and Kim Y, et al. "Direct comparison of human mesenchymal stem cells derived from adipose tissues and bone marrow in mediating neovascularization in response to vascular ischemia." *Cell Physiol Biochem* 20(6) (2007) 867-876.

However, it has been shown that the phenotype of plastic adherent adipose derived cells changes with cell culture and is influenced by culture conditions. (Gimble J and Guilak F "Adipose-derived adult stem cells: isolation, characterization, and differentiation potential" *Cytotherapy* 5(5) (2003) 362-369; Boquest A C, et al "Isolation and transcription profiling of purified uncultured human stromal stem cells: Alteration of gene expression after in vitro cell culture" *Mol. Biol. Cell* 16(3) (2005) 1131-1141).

As used herein, "reparative cell population" refers to a mixture of cells that includes "tissue engrafting cells" that are herein defined to include MSC as well as cells such as fibroblasts and endothelial cells that are able to proliferate and engraft a target tissue when returned to the body. The reparative cell population may also include one or more "supportive cell" populations. Supportive cells are herein defined as cells that do not permanently engraft in the target tissue but may aid in the tissue remodeling process that is essential to healing of damaged tissue. These may include, for example, lymphocytes and macrophages. As used herein the term "reparative cell population" is not limited to plastic adherent cells and may be the same as adipose stromal vascular fraction cells under some circumstances.

Advantageously, such reparative cell preparations can be utilized for cell therapy without prior expansion in cell culture. Prerequisite for such a procedure is the requirement to obtain a sufficient number of cells for therapeutic use without expanding the cells in culture. Subcutaneous tissue may provide as many as 300,000 reparative cells per gram, which have an appropriate cell type composition. In contrast to the prevailing view that a single cell type is optimal for cell therapy, the present inventors believe that multiple cell types are able to act in a coordinated manner to achieve healing and/or repair. Thus, in one embodiment a heterogeneous reparative cell population is provided to mediate a tissue healing and repair process that emulates endogenous repair.

In the present invention, "progenitor cells" generally refer to uncommitted mesenchymal stem cells in various mesenchymal tissues, such as muscle, bone, cartilage and adipose tissue and vascular progenitor cells that can be differentiated into vascular cell types. Such cells are generally believed to constitute a cellular reserve fraction and function as target engrafting cells.

The present invention may be utilized in a process for the isolation of cell populations without loss of cells that would otherwise be useful but lack a property of being strongly adherent when first removed from the body. For example, when plated onto plastic, adherence of non-fibroblast cells in a fresh cell preparation may require several hours to more than one day. Culture of the fresh cell preparation changes two characteristics. First, monolayer culture enhances certain cell populations resulting in a cell preparation that is distinct from the fresh isolate. Second, culture in an adherent monolayer selects and conditions the cells for adherence, so that upon passaging and replating the resulting cell populations adhere much more rapidly (i.e., <30 min) Isolation of MSC involves plastic adherence by definition and eliminates non-adherent and weakly adherent cells in spite of their beneficial properties.

To have clinical utility as a point of care product, the present inventors believe that cell seeding onto a matrix or scaffold for implantation would be preferably accomplished in <about 2 hours and more preferably in < about 1 hours. In other embodiments, matrices are provided that are adapted to provide rapid, adherence or incorporation of select constituent subpopulations of reparative cells such that cell selection can be performed at the point-of care.

In one embodiment of the invention a method of modifying the surface of a biocompatible matrix or scaffold is provided to enable selective, rapid adherence of freshly prepared reparative cells, stem cells, or progenitor cells. In one embodiment the selective adherence occurs in an incubation time frame of < about 2 hours. If desired, following incubation, non-adherent, undesirable cells are removed with a wash step prior to implantation of the seeded matrix. In one embodiment of the invention, modifications such as coating of matrices and/or chemical or physical modifications are undertaken such that the matrix has increased selectivity for freshly isolated reparative cells over a contact time of ≤1 hour. If desired, unbound cells may be removed by washing. In one embodiment of the invention, a method is provided that includes assembling a biocompatible matrix to create a three dimensional topology that enhances selective, rapid adherence of freshly prepared reparative cells, stem cells, or progenitor cells. Rapid adherence is herein defined as adherence occurring in a time frame of < about 2 hours.

In one embodiment of the invention, the biocompatible matrix comprises one of more of: collagen, PLGA, PGA, silk fibroin, chitosan, polypropylene, acellular skin preparations of human or other animal origin, and hyaluronic acid polymers (i.e. HYAFF®-11 sponges). The matrices may be used without coating or may have surface modifications including coating with specific cell adhesion compounds such as hyaluronic acid, fibrin, collagen, fibronectin, antibodies, aptamers, or thioaptamers, chemical etching such as with NaOH, coatings such as iridium oxide, and/or manufacturing processes that alter the surface topology of existing matrices to increase surface roughness or textural structure.

The following examples are included for the sake of completeness of disclosure and to illustrate the methods of making the compositions and composites of the present invention as well as to present certain characteristics of the compositions. In no way are these examples intended to limit the scope or teaching of this disclosure.

Isolation of Reparative Cells from Adipose Tissue:

In contrast to prior isolation methods, the present invention provides for isolation of reparative cell populations without the use of centrifugation or plastic adherence, and which is suitable for use at the point of care. In one embodiment of the invention, population of cells for cell transplantation is prepared by dissociating a sample of donor adipose tissue into individual cells and small clusters of cells until the dissociated cells and clusters of cells are reduced in diameter to about 1000 microns or less, phase separating the individual cells and small clusters of cells into an aqueous cellular layer and a lipid layer without centrifugation, and collecting cells for cell transplantation from the aqueous cellular layer.

In one embodiment of the invention the phase separation is undertaken by introducing the dissociated cells, including adipocytes, into a lipid separating unit in an aqueous medium. The lipid and lipid containing adipocytes float upward, thus forming a top lipid layer in the lipid separating unit while the non-lipid containing or non-adipocyte cells float downward under the influence of normal gravity and are withdrawn from under the top lipid layer. In accordance with this method, non-adipocytes can be separated from lipid containing cells without centrifugation.

In one particular embodiment of the invention, as figuratively depicted in the flow chart of FIG. 1, adipose tissue is introduced into a digestion chamber that includes a digestion fluid and an internal digestion mesh and the tissues and digested cells are recirculated across the digestion mesh until the tissue is separated into a digestion mixture that includes individual cells and small cell clusters, followed by phase separating the digestion mixture through an aqueous medium disposed in a lipid separation unit. After the phase separation separates the constituent cells of the digestion mixture on the basis of density in an aqueous medium, desired cell populations are collected from select regions within the lipid separation unit. Isolation of desired cell populations is preferably accomplished in a unitary device without a need for centrifugation. In further embodiments, the digestion mixture is filtered over at least one dispersing filter prior to phase separating. In certain embodiments the digestion mixture is finally conveyed through a dispersing head that is disposed within and forms an entry port to the lipid separating unit. The dispersing head further divides clumps of cells within the digestion mixture as the digestion mixture enters the lipid separation unit. The method is particularly suitable isolation of cells from adipose-containing tissues of human, equine, canine, feline, simian, caprine, and ovine origin.

Various embodiments of the present invention provide a reparative cell preparation for cell therapy, wherein the cell preparation comprises a heterogeneous mixture of tissue engrafting cells and supportive cells that is derived without prior expansion in cell culture. Once derived, cell preparations of the present invention can optionally undergo further treatment prior to use for cell therapy. For instance, in one example, leukocytes within the cell preparation may be removed. In further examples, cell preparations of the present invention are seeded (i.e., applied) onto a biocompatible matrix and are then suitable for implantation at the point-of-care. Such biocompatible matrices can include without limitation scaffolds, grafts, sponges, and other well known materials that may be surgically implanted into the subject.

Example 1

Reparative Cell Collection Apparatus

Figure 6:
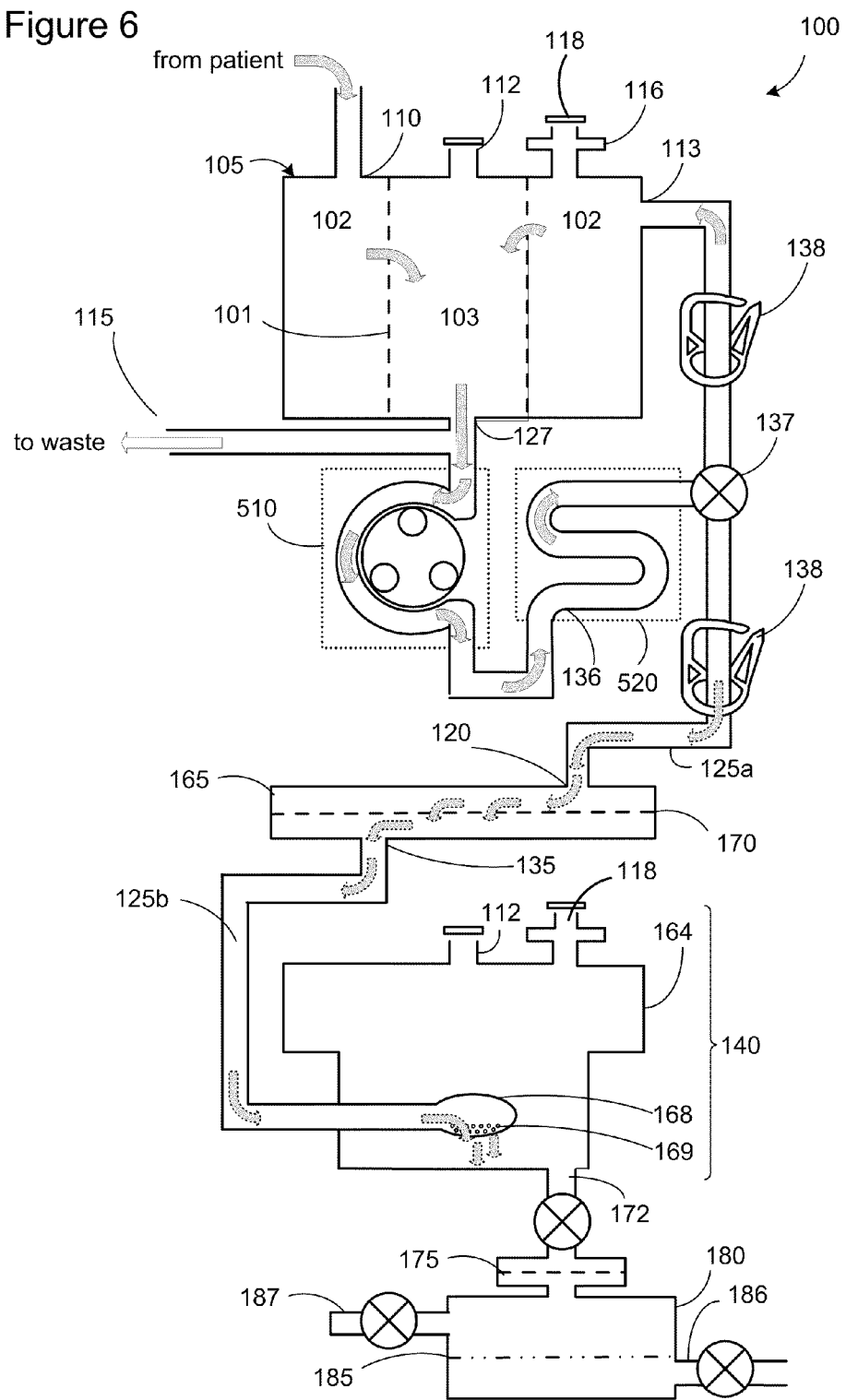
FIG. 6 is a figurative diagram of one embodiment of a cell separation apparatus.

FIG. 6 is a schematic depiction of one embodiment of a unitary apparatus for isolation of stromal vascular cells, wherein the cells are collected without centrifugation. Apparatus 100 includes a digestion chamber 105 and a fat separation chamber (a.k.a. lipid separation unit) 140. Digestion chamber 105 generally refers to a housing that can receive and treat a biological sample and can have various shapes and structures. The depicted digestion chamber 105 includes at least two compartments, predigestion chamber 102 and post digestion chamber 103, separated by digestion mesh 101. The digestion chamber may optionally include a vent 116 that may include a filter 118 to preserve sterility such as, for example, an ACRODISC brand syringe filter (Pall Scientific). In the depicted embodiment, the digestion chamber 105 is cylindrical and the pre and post digestion chambers are formed by placement of an inner mesh cylinder 101 disposed within the digestion chamber. The porosity of the digestion chamber mesh is selected based on various desired properties including but not limited to a size sufficient for small clusters of digested tissue to pass through the mesh without rate limiting clogging of the mesh. In one embodiment the digestion mesh has a plurality of holes or pores having an opening size of approximately 2-0.5 mm. In one embodiment found to be effective, the mesh is a nylon mesh having an average pore size of approximately 1 mm.

Adipose tissue in extraction fluid or tumescent is introduced via entry port 110 into predigestion chamber 102. The extraction fluid or tumescent is able to drain through mesh 101 and out drain port 127 and ultimately to waste port 115 for discard. Valves 137 and/or clamps (not shown) control the pattern of flow, as well as the action of pump 510. After draining of the extraction fluid and optional washing if desired, a digestion buffer is added to the predigestion chamber via a fill port such as fill port 112 and a digestion enzyme or cocktail of enzymes is added to the predigestion chamber. The enzyme can be added together with the digestion buffer if desired. In one embodiment found to be effective, the buffer solution utilized was a lactated Ringer's solution, however other physiologic buffers are suitable and are readily envisioned by one of skill in the art. In the depicted embodiment, the enzyme may be added through a dedicated port such as fill port 112, which may be constructed in any number of ways including for example as a valvable opening or as a self-sealing septum. Optionally, a compound such as a poloxamer may be added to improve flow and as an aid in maintaining cell viability. For example, poloxamer 188 may be used at concentrations ranging from about 0.05% (w/v) to about 5% (w/v). Further, heparin or low molecular weight heparin may be added at concentration ranging from 1-100 U/ml, preferably between 10-30 U/ml, to reduce formation of clot like clumps and recovery of a unicellular suspension.

A digestion period is then begun wherein the digestion mixture is recirculated, typically through the action of a pump such as for example roller or peristaltic pump 510. The direction of flow is from predigestion chamber 102 through digestion mesh 101, into post digestion chamber 103, out drain port 127, and back around into the predigestion chamber through recirculation port 113. This configuration provides ample volume for both chambers and, as can be seen by the depicted arrows, the digestion mixture is able to circulate around as well as through the digestion mesh 101.

As part of the recirculation loop the digestion mixture may be passed through a heat exchanger loop 136 by the action of pump 510. In a preferred embodiment, equipment such as pump 510 and heating element 520, shown surrounded by dashed lines, are adapted to be operably attached to apparatus 100 via tubing but are part of a reusable base unit that constitutes capital equipment in contrast to apparatus 100, which is designed for clinical use to be a disposable unit that does not require any electrically operable components and can be supplied as a presterilized single use unit. The heat exchanger loop 136 is heated by heating element 520 which provides controlled heating to the heat exchanger loop for optimum enzyme activity. As digestion continues an increasing greater proportion of the adipose tissue is able to cross the digestion mesh 101. In a preferred embodiment, the apparatus 100 is agitated by shaking during the digestion period. After the adipose tissue is sufficiently digested, the recirculation loop is ceased and the digestion mixture is directed to fat or lipid separation unit 140. In alternative embodiments, modulation of processing temperatures, for example to control the activity of digestion enzymes, is provided by enclosing the processing apparatus in a thermally controlled chamber. Such a thermally controlled chamber may be used together with, or in lieu of, use of one or more heat exchanger loops.

In one embodiment, prior to allowing the digestion mixture to enter the lipid separating unit, the unit is prefilled with a separation buffer. In further embodiments of the present invention, various compositions may be introduced into a lipid separating unit to aid in phase separation. For instance, the separation buffer may comprise separation facilitating compounds that may be introduced into lipid separating unit 140.

The separation buffer may be added through various mechanisms. In the depicted embodiment, a fill port 112 is provided for separation buffer addition. In the lipid separation unit 140, phase separation occurs and the lipid and lipid containing cells float up through the separation buffer as depicted by the upward directed thick dashed arrow and ultimately form a floating lipid phase. The non-lipid containing cells, including a reparative cell population, settle down. After a desired period wherein the lipids have had time to migrate to the top of the chamber, the underlying phase is removed via collection port 172. In the embodiment provided in FIG. 6 flow patterns are depicted with the recirculation of tissue during digestion depicted in solid lined arrows while the digested mixture is depicted in dashed lined arrows. In the depicted embodiment, apparatus 100 further includes a dispersing head 168 having a plurality of pores 169 as the entry port of fat or lipid separating chamber 140. In one embodiment, the average pore size of the dispersing head is in the range of about 0.3 mm (300 microns) to about 1 mm (1000 microns), while in another embodiment the average pore size is from about 0.4 mm (400 microns) to about 0.6 mm (600 microns). In one embodiment, the dispersing head has an average pore size of about 0.5 mm (500 microns).

In the depicted embodiment of FIG. 6, dispersing head 168 is a substantially rigid structure designed to be located relatively close to the bottom of the lipid separating unit 140. As depicted, the dispersing head can be directed with its exit openings or pores 169 facing downward such that the fluid flow entering lipid separating unit 140 is in the opposite direction of the buoyancy of lipid-filled cells and thus further reduces clumps and releases reparative cells trapped together with lipid-filled adipose cells. Use of the dispersing head has been shown by the present inventors to result in greater yield of reparative cells.

In the embodiment depicted in FIG. 6, a further dispersing filter chamber 165 including dispersing filter 170 is included in-line prior to the dispersing head 168 and is adapted to further divide clumps of cells and to protect the dispersing head from clogging. In one embodiment, the dispersing filter is dimensioned to have a pore size ranging from about 0.2 mm (200 microns) to about 0.3 mm (300 microns). In yet another embodiment, the dispersing filter has an average pore size of about 0.25 mm (250 microns). However, one of ordinary skill in the art will recognize other suitable filter sizes that can be used in the present invention. Furthermore, one of ordinary skill in the art will recognize that dispersing filter 170 can be in other forms or may, in some embodiments, be eliminated entirely depending on the configuration of the apparatus.

Likewise, one of ordinary skill in the art will recognize that container 105 can have various other shapes and arrangements. As with other embodiments, digestion chamber 105 is in fluid communication with the lipid separating unit 140, and any intervening filters, via a tubing network. The pattern of flow is controlled by one or more valves 137 and/or clamps 138 as well as the action of the pump. The embodiment depicted in FIG. 6 includes a separate waste line 115.

As depicted in FIG. 6, the upper most portion 164 of the lipid separating unit may have a greater diameter than the lower portion to accommodate the floating fat layer. The embodiment depicted in FIG. 6 also includes an optional seeding chamber 180, which may include a cell seeding substrate or scaffold 185. Such a seeding chamber may serve various functions. In one embodiment, the chamber can contain the aforementioned substrate or scaffold on which cells might be seeded as liquid is drained from the lipid separating unit. In operation, reparative cells collected using the apparatus can be directly disposed onto the cell seeding substrate and either implanted on the patient or removed to an incubator for further cellular expansion. In another embodiment, the chamber might be adapted to allow buffer exchange. In further embodiments of the present invention, chamber 180 may be entirely absent or may be provided as a separate apparatus. In some of such embodiments, lipid separating unit 140 may have a port and/or an opening for passage of separated material.

In another embodiment, various chamber and compartment of the apparatus might contain materials such as antibodies or aptamers or thioaptamers that could be used to negatively select for materials to be removed from the processed material for further purification. Cell selection agents that may be introduced into containers of the present invention generally refer to one or more compounds for positive cell selection or negative cell selection. For negative cell selection, such cell selection agents may aid in the depletion of various cells from a biological sample, such as the depletion of leukocytes and/or erythrocytes in one embodiment. For positive cell selection, the cell selection agents may specifically bind a desired cell type for isolation. Cell selection agents suitable for use in the present invention may include, without limitation, an antibody (see U.S. Pat. Nos. 6,491,918, 6,482,926, 6,342,344, 6,306,575, 6,117,985, 5,877,299, and 5,837,539), an aptamer (see U.S. Pat. No. 5,756,291), and/or a thioaptamer (see U.S. Pat. No. 6,867,289), for example, all of which are incorporated herein by reference in their entirety. In some embodiments, the cell selection agents may also be immobilized on the matrix or scaffold 185.

As depicted in FIG. 6, the lipid separating unit may optionally include fill port 112 and a vent port 116 with sterility filter 118. An additional collected cell filter 175 may be optionally included prior to the seeding chamber 180 and may be adapted to optionally provide for purification and sizing of desired cells as well as to prevent clogging of downstream components. Collected cell filter 175 is generally a circular structure in the present example, though a person of ordinary skill in the art could envision other shapes and structures.

In the example shown in FIG. 6, collected cell filter 175 is desirably a filter with a pore size of less than about 250 microns. However, in other embodiments, collected cell filter 175 can have a pore size ranging from about 0.01 mm (10 microns) to about 0.1 mm (100 microns). In another embodiment, collected cell filter 175 can have a pore size ranging from about 0.03 mm (30 microns) to about 0.05 mm (50 microns). In a further embodiment, the average pore size in collected cell filter 175 is about 0.037 mm (37 microns). In additional embodiments, the collected cell filter may be entirely absent.

Example 2

In one example, a reparative cell population was isolated as follows. Lipoaspirate was collected under informed consent in the operating room directly into a unitary purification apparatus by standard suction assisted lipoplasty with tumescent. The apparatus including tumescent fill was transported to the laboratory and processed within 2 hours of collection. In practice however, it is anticipated that the purification apparatus will be suitable for, and will be used, in the operating suite. The digestion chamber of the apparatus as depicted in Example 1 included a predigestion chamber and an inner postdigestion chamber separated by a nylon mesh having a pore size of approximately 1 mm. The tumescent was drained and a volume of approximately 100 ml of drained lipoaspirate was washed by draining the predigestion chamber and refilling with a solution of lactated Ringer's solution, which was prewarmed to 37° C. containing a proteolytic enzyme combination comprised of collagenase IV (60,000 U) and dispase (120 U). An additional 150 ml of lactated Ringer's was added to the lipid separating unit. The digestion recirculation loop was implemented by a pump actuated flow path from the predigestion chamber into the postdigestion chamber and including passage across a heat exchanger that maintains the digestion mixture at approximately 37° C. Recirculation was continued for approximately 30 to about 60 minutes or until greater than 90% of the cellular volume of the predigestion chamber was able to pass the 1 mm mesh into the post digestion chamber. The design of the pre and post digestion chambers, separated by the nylon mesh across which the recirculation flow path passes repeatedly, provided trapping of connective and other debris tissue on the digestion mesh. After digestion was sufficiently complete, the digestion mixture was pumped tangentially over a nylon dispersing filter having a pore size of 250 µm. The filtered digestion mixture was then pumped into a columnar lipid separating chamber that was integral to the apparatus. As previously mentioned, the lipid separating chamber was prefilled with a volume of 150 ml lactated Ringer's solution prior to introduction of the digestion mixture such that when the filtered digestion mixture entered the chamber, any clusters of cells including lipids or adipocytes, were subject to fluid shear as the lipid moieties float upward in the aqueous solution. The filtered digestion mixture entered the lipid separating chamber through a dispersing head having a plurality of downwardly directed pores with a pore size of 500 µm and disposed proximally to a bottom inner surface of the lipid separating unit. The design was adapted for forcibly flowing the cell mixture against an inner surface within the lipid separating unit and thereby further disrupting cell clusters within the cell mixture prior to fluid phase separation. Fluid phase separation was allowed to proceed at room temperature for about 5 to about 30 minutes prior to collection of the stromal vascular fraction from the bottom of the lipid separating chamber.

Example 3

After processing tissue in the device, cell viability and cell number were determined. In one processing run, the collected cells were plated at a density of approximately $7 \times 10^5$ cells/cm$^2$ into a T185 flask in MEM, 20% (v/v) FBS including and antibiotic/antimycotic and cultured overnight at 37° C. in a humidified 95% $O_2$, 5% $CO_2$ atmosphere. After overnight, non-adherent cells were harvested by aspiration, and adherent cells were harvested by trypsinization. Immediately after harvest, cells were processed for flow cytometry. Numbers represent the net percentage positive cells after subtraction of background (2' Ab only) and gating to remove debris. FIGS. 2A and B represent data from two processing runs.

Cells collected as described in Example 2 have also been characterized by direct analysis without separation into adherent and non-adherent populations. The results are depicted in FIG. 3.

In comparing the cells isolated as disclosed herein with mesenchymal stromal cells isolated using centrifugation and plastic adherence in accordance with conventional preparation methods, several notable differences are apparent. Mesenchymal stromal cells have been classically isolated from adipose tissue using enzymatic digestion, centrifugation to remove lipid filled cells and plastic adherence with culture in vitro. These cells show a fibroblast-like morphology. Although the cells are initially heterogeneous, the phenotype of population changes in culture including loss of CD31+, CD34+, CD45+ cells, and an increase in CD105 and other cell adhesion type molecules. Generally, <10% of the cells express markers associated with stemness (e.g., CXCR4, sca-1, SSEA-4) and a substantial fraction differentiates into adipocytes in inductive media. A lesser fraction differentiates into other lineages (bone, cartilage, nerve) in inductive media.

The reparative cell population isolated as disclosed herein without centrifugation or plastic adherence is also a heterogenous population and generally <10% express markers associated with stemness (e.g., CXCR4, Sca-1, SSEA-1, SSEA-4, VEGFr2, CD117, CD146, Oct4). However, a substantial fraction of the early multipotent stem cells are not plastic adherent. Importantly, a substantial fraction of cells expressing markers of stemness, endothelial cell lineages and/or exhibiting a small diameter 6 mm) are not adherent and are lost using conventional isolation methods that rely on plastic adherence or centrifugation.

Example 4

Cells were collected as essentially described in Example 2. Digestion with warming, agitation, and recirculation was conducted for 30 minutes. The resulting slurry was then pumped through a 250 µM filter and into the lipid separating unit. After a 10 minute static hold, the lower aqueous phase was collected, and cells from this phase were concentrated by centrifugation at 400×g before characterization. Cell yield was determined by counting with a hemacytometer. Cell viability was assessed by two assays, trypan blue exclusion using phase contrast microscopy and the Live/Dead assay (InVitrogen, Inc) using a Coulter Epics XL-MCL cytometer.

Collected cells were characterized by cytometry using cell surface markers CD31, 34, 44, 45, 71, 73, 90, 105, 117, 146, SSEA-4, and Sca-1. All assays were performed using a Coulter Epics XL-MCL cytometer. Cell preparations were plated in standard growth medium and cultured overnight in a humidified, 37° C., 95% $O_2$, 5% $CO_2$ environment. Non-adherent cells were removed by pipette, and adherent cells were detached by trypsinization. Cells were layered onto ficoll and centrifuged at 1000×g to remove erythrocytes prior to incubation with primary antibody. Adherent and non-adherent cell populations were analyzed separately, and then an estimate for surface marker profile in the total population was calculated from cell counts and surface marker profiles in the adherent and non-adherent populations. All assays were performed with murine anti human antibody specific for the target in question and FITC conjugated goat anti murine secondary antibody.

Culture characteristic assays were performed as follows. For determination of doubling time, $1 \times 10^6$ adherent cells from overnight culture were seeded in a 75 cm$^2$ flask and cultured for 4~5 days with medium changed every 2 days. Cells were harvested by trypsinization and counted with a hemacytometer. Doubling time was calculated based on cell count versus the number of cells plated. For determination of colony forming units (CFU), $3.1 \times 10^5$ cells were suspended in 3.1 ml growth media (MEM, 20% FBS, antibiotic/antimycotic). Duplicate dilutions of cells were prepared and plated at approximately $2.8 \times 10^4/cm^2$, $0.5 \times 10^4/cm^2$, and $0.1 \times 10^4/cm^2$ in 6 well plates. Cells were maintained in a humidified 37° C., 95% $O_2$, 5% $CO_2$ environment, and media was changed 2x/week. Colony forming units were scored after 7-14 days in culture. Cells were fixed and stained with hematoxylin and pictures were taken under the microscope from 5 fields per well at 25× magnification for quantitation. Colonies with at least 10 fibroblast-like fusiform cells clustered or piled together were counted. For colonies on the edges of a microscopic field, only those that were judged to be more than 50% within the field were included in the calculations. Percent colony forming units was calculated from the number of colonies relative to the total number of cells plated and averaged across the three dilutions.

Results for subject demographics, cell yield, doubling time and CFU are presented in FIG. 4. Mean total cell yield was $30 \times 10^6$ cells from the 8 tissue samples processed in the device described in Example 1. Cell yield for the two samples from male subjects averaged $13.5 \times 10^6$ whereas cell yield from the 6 female subjects averaged $36.9 \times 10^6$. Mean cell viability was 82 and 83 percent for the two respective assays. Mean percent CFU was 12%, ranging from 6.6 to 15.4.

Results for surface markers are presented in FIG. 5. Surface markers for endothelial cells (CD31), hematopoietic progenitor cells (CD34), leukocytes (CD45), mesenchymal stromal cells (CD44, CD73, CD90) and progenitor cells (CD117, CD146, Sca-1, and SSEA-4) were observed in all specimens. The high yield and viability of the diverse population is considered by the inventors to be important contributions provided by the method and apparatus of the invention.

Scaffolds

In one embodiment of the invention, reparative cells are localized onto a scaffold such that upon implantation a locally high concentration of reparative cells, including stem cells, is retained at the implantation site. A number of biocompatible materials including biodegradable materials are known. Available biocompatible materials include polytetrafluoroethylene (PFTE), woven polyester (i.e. Dacron® fabric), open foam silicone encased in microporous expanded PTFE (Evera Medical), stainless steel, polypropylene, polyurethanes, polycarbonates, nickel titanium shape memory alloys (i.e. Nitinol) and cobalt-chromium-nickel alloys (Elgiloy). Although the synthetic patches are not absorbed, they act as a scaffold onto which normal tissue can grow and cover the defect, which is essentially "scarred" into place after about 3-6 months depending on the conditions of the defect. In addition to non-absorbable biocompatible materials, there is a whole range of degradable and bio-absorbable biomaterials that are suitable.

In one embodiment, biomaterials are seeded including, for example, silk fibroin-chitosan, acellular dermal matrices (ADM) derived from normal human skin, preformed biodegradable scaffolds composed of polyglycolic acid (PGA) and poly L-lactic acid (PLLA) (i.e. Vicryl® polyglactin woven mesh), and bioabsorbable scaffolds coated with extracellular matrix (i.e. Dermagraft® polyglactin woven mesh coated with extracellular matrix (ECM) laid down by fibroblasts prior to cryopreservation). In one embodiment of the invention, a bioabsorbable three-dimensional scaffold composed of ECM is used as the cell scaffold for the freshly isolated reparative cells of the invention.

Treatment of the surface of the scaffold, such as with the above NaOH etching, can increase the adherence of stem cells. It has been determined by the present inventors that a local micro-roughness and the creation of niches increases not only the adhesion but also enhances the three dimension incorporation of stem cells into the material. The micro-roughness of the surface structure can be increased by mechanical processes including by embossing, blasting, such as particle blasting, or by plasma etching, controlling the polymerization processes, heat application, by chemical etching, and including by printing such as by inkjet printing.

Where it is desired to increase the surface roughness of the matrix, a micro-rough surface is generated wherein three dimensional mounds of scaffold material or peaks, valleys and voids are arrayed to provide surface irregularities at a periodicity of 1-100 µm. In one embodiment the three dimensional mounds are formed as ridges while in other embodiments the three dimensional mounds are hemispherical. In other embodiments a pattern of ridges and hemispherical mounds is formed. Alternatively, or in addition, a spongy surface characterized by voids is provided.

In one embodiment of the invention, scaffolds are provided that are characterized by a spongy texture formed by subjecting the nascent scaffold material to a partial vacuum during polymerization or drying. Desolved gases in the uncured scaffold solution expand and form bubbles that are induced to rupture just as curing is completed thus forming a plurality of voids and pockets that together result in a sponge like composition having a vastly increased surface area. In one embodiment, the formation of bubbles is enhanced by inclusion of a frothing agent into the uncured scaffold material such that bubble formation is enhanced by application of the vacuum.

In the case of printing such as with inkjet type printing, an array can be deposited according to a programmed pattern including patterns forming a plurality of surface structures. In other embodiments, printing such as with inkjet type printing is further utilized to apply a plurality of different substrate materials and/or growth factors arrayed on the surface thus promoting the growth of disparate cell types in a virtual tissue pattern.

Collagen:

Collagen is another biomaterial that is suitable for use with mixed reparative cell populations, both for the process for the selection and adhesion of stem cells, and as a local carrier and matrix or as an adhesion matrix when coated onto other materials. FDA approved Type 1 collagen products, such as those available from Collagen Matrix, Inc., Franklin Lakes, N.J., are commercially available. Such collagens are especially useful for external application such as non-healing wounds and burns, soft tissue defects, cosmetic surgery, and for nerve repair wherein a collagen sleeve serves as a conduit between the interrupted nerve ends.

Bioresorbable Silica Gel Matrix:

In another embodiment, a very recently developed bioresorbable silica gel matrix is seeded with fresh reparative cells. The matrix of silica gel fibers, developed by Dr. Jörn Probst and Dipl.-Ing. Walther Glaubitt at the Fraunhofer Institute for Silicate Research ISC in Würzburg, is shape-stable, pH-neutral and 100 percent bioresorbable. The fibers are produced by means of wet-chemical sol-gel process in which a transparent, honey-like gel is produced from tetraethoxysilane (TEOS), ethanol and water in a multi-stage, acidically catalyzed synthesis process. The gel is processed in a spinning tower which produces fine endless threads which are collected on a traversing table and spun in a specific pattern to produce a multi-layer textile web which can be cut to desired size and sterilized prior to loading into a seeding chamber.

Highly pliable biomaterials loaded with reparative cells can be locally wrapped around the tissue or inserted into a tissue defect where it is desirable to localize cells for repair at an increased local concentration. This is especially useful where the scaffold can be integrated surgically into the defect when carrying cells for nerve repair, wrapping around non-healing bone fractures, ruptures or injuries to tendons, which normally show a very slow rate of healing, applications in repair of cartilage defects in joints or of scars and injuries to skin and the underlying tissue and also for plastic, cosmetic, aesthetic repair. In addition, a repair such as an entubulation, or a wrapping around of venous structures, lymphatic vessels, and nerves is also a target of the cell loaded scaffolds disclosed herein.

Acellular Dermal Matrix Scaffolds:

In one embodiment of the invention, acellular dermal matrix (ADM) pre-seeded with reparative cells prior to implantation is provided for treatment of soft tissue injuries including abdominal wall compromise and soft tissue loss secondary to traumatic and oncologic processes. Human acellular dermal matrix (ADM) has become widely used in plastic surgery because it is non-immunogenic, mechanically robust and has favorable handling characteristics. Recent reports have suggested that the post-engraftment mechanical behavior could be enhanced by cell seeding. (Erdag G, Sheridan R L. "Fibroblasts improve performance of cultured composite skin substitutes on athymic mice" *Burns* 30(4) (2004) 322e8; Fuchs J R, et al. "Diaphragmatic reconstruction with autologous tendon engineered from mesenchymal amniocytes" *J Pediatr Surg* 39(6) (2004) 834e8). Additionally, others have shown that seeding adipose-derived stromal cells on a carrier bioprosthetic material facilitated new bone formation in the treatment of a bony defect. (Cowan C M, Shi Y Y, Aalami O O, Chou Y F, Mari C, Thomas R, et al. "Adipose-derived adult stromal cells heal critical-size mouse calvarial defects" *Nat Biotechnol* 22(5) (2004) 560e7). Thus, a cell-seeded matrix is believed to offer some benefits for introducing cells to the local environment as it provides a framework for the support of their regenerative capacity. ADM provides a three-dimensional scaffold into which seeded cells could incorporate and help to build the foundation for the integration of local tissue with the graft.

Example 5

Human adipose tissue was obtained from elective body contouring procedures and the tissue digested with a solution of 0.07% Blendzyme 3 (F. Hoffman-La Roche Ltd, Basel, Switzerland) with mild agitation at 37° C. for 60 minutes. The digest was passed through a 100 µm filter, then through a 40 µm filter and finally though a 10 µm filter. The filtered material was centrifuged at 1500 RPM for 10 minutes and resuspended in 1× PBS. Following a second centrifugation the cells were resuspended in MEM containing 20% FBS, 2 mM L-glutamine, 100 U/ml penicillin, and 100 µg/ml streptomycin and selected based on adherence to T75 tissue culture flasks for 24 hours after which non-adherent cells and debris were discarded by aspiration. Adherent cells were incubated in a 5% $CO_2$-containing chamber at 37° C. with medium changed every 3 days. ADSCs between passages 1 and 6 were used for all experiments.

For seeding of the grafts, six-mm diameter ADM pieces (Alloderm® Lifecell) having a thickness of 0.53-0.76 mm were placed completely covering the well bottom in 96-well plates with the papillary dermal surface facing up and the grafts were covered with 200 µl aliquots of medium alone in the ADM group and with equal volume of cell suspension containing $1 \times 10^5$ ADSC in ADSC-ADM group. Grafts were incubated under standard culture conditions for 24 hours after which overlying medium or cell suspension was aspirated. The grafts were flipped to place the opposite reticular dermal surface facing up, and the corresponding medium or cell suspension solution was placed on the other side. Grafts were then incubated for 24 hours and transferred to the operating suite for surgical engraftment.

Figure 11:
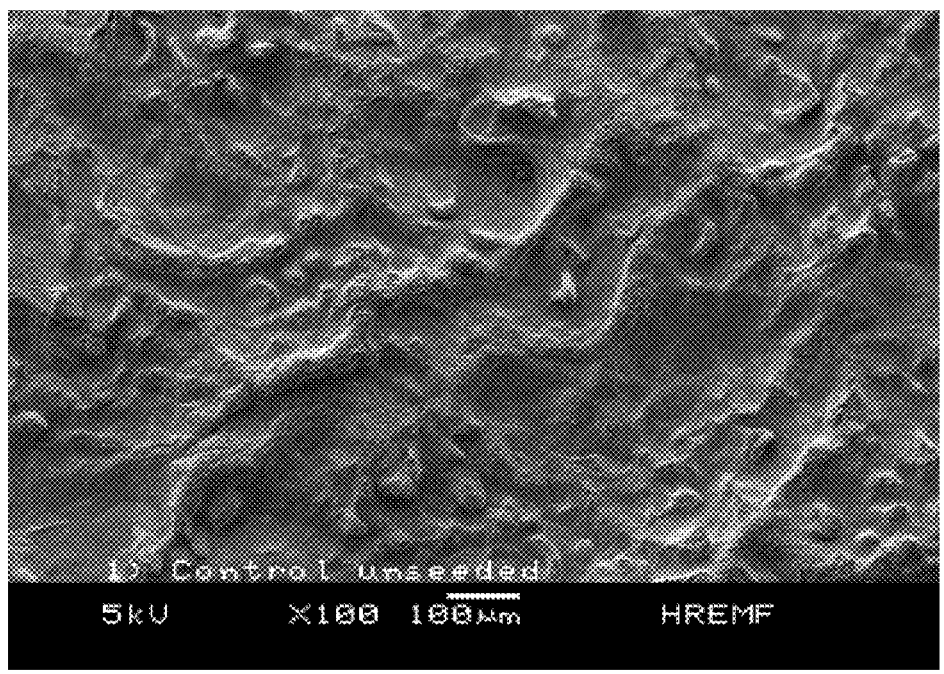
FIG. 11 is a Scanning Electron Micrograph (SEM) of an unseeded Acellular Dermal Matrix (ADM) at 100× magnification.
Figure 12:
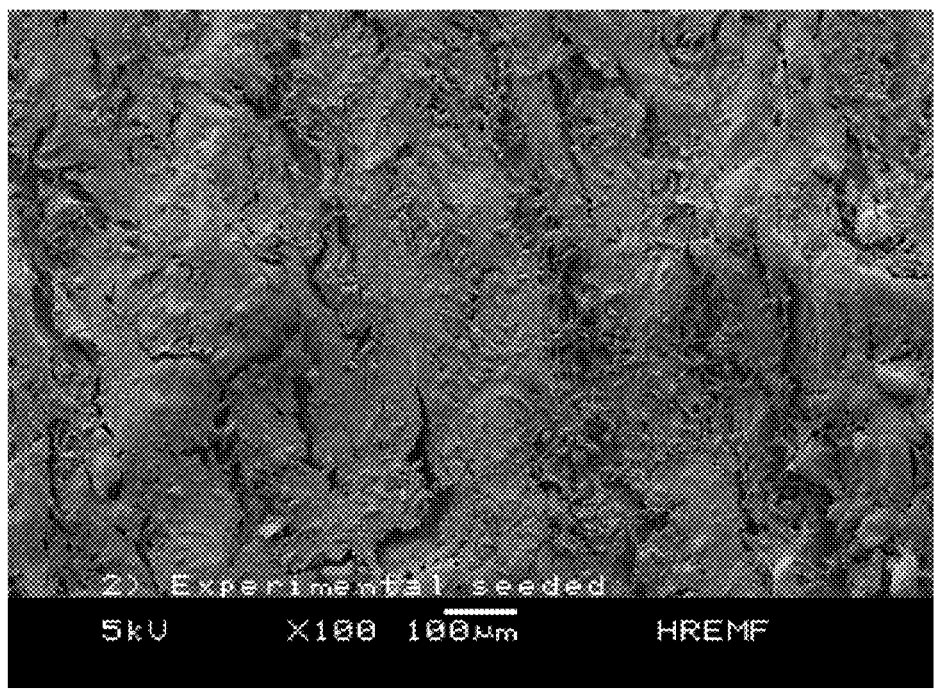
FIG. 12 is a SEM of an ADM seeded with adipose derived stromal cells (ADSC) at 100× magnification.
Figure 13:
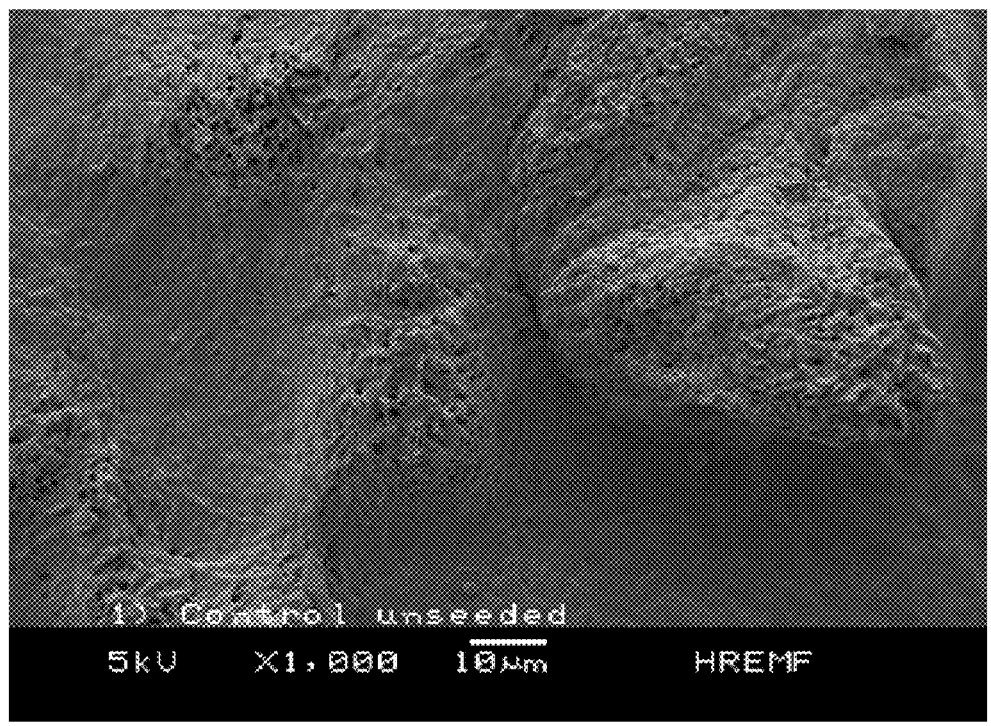
FIG. 13 is a SEM of an unseeded ADM at 1000× magnification.
Figure 14:
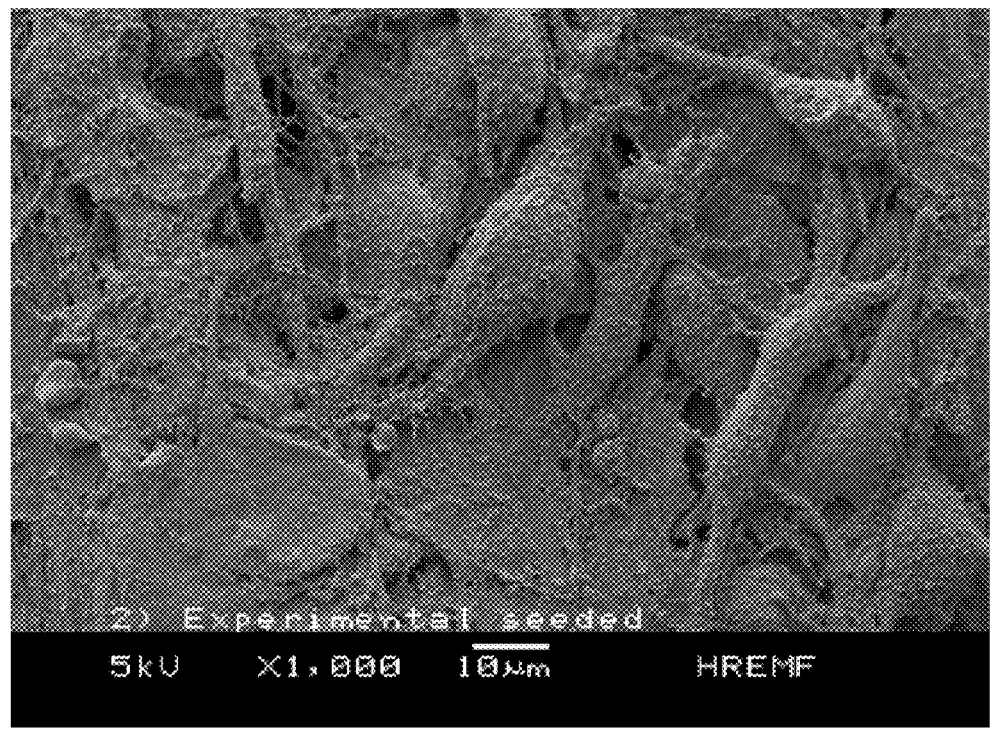
FIG. 14 is a SEM of an ADM seeded with ADSC at 1000× magnification.
Figure 15:
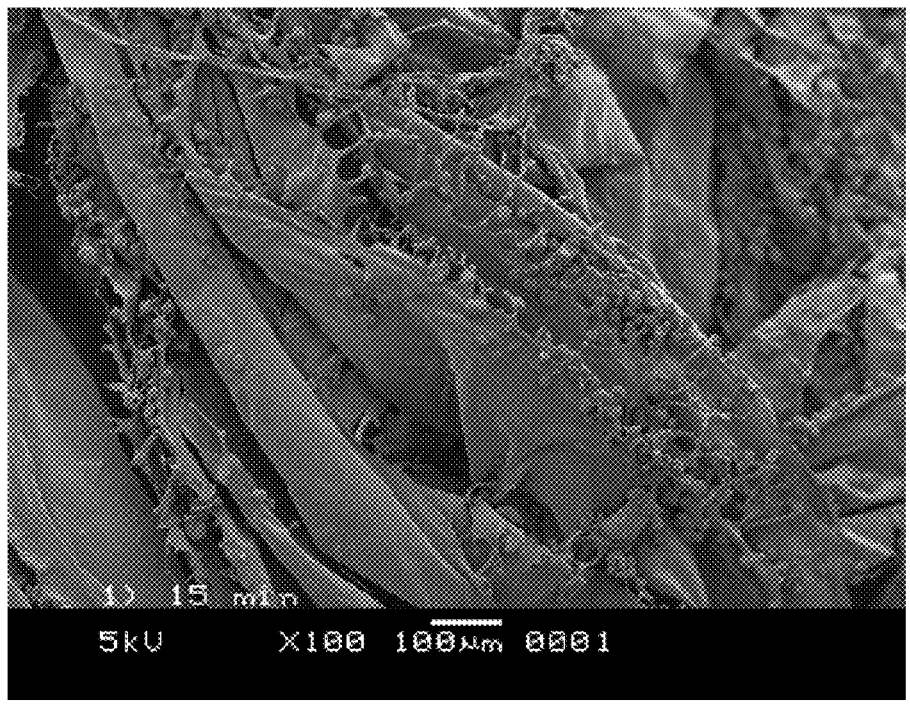
FIG. 15 is a SEM of a silk fibroin-chitosan scaffold (SFCS) seeded with adipose derived stromal cells (ADSC) at 100× magnification.
Figure 16:
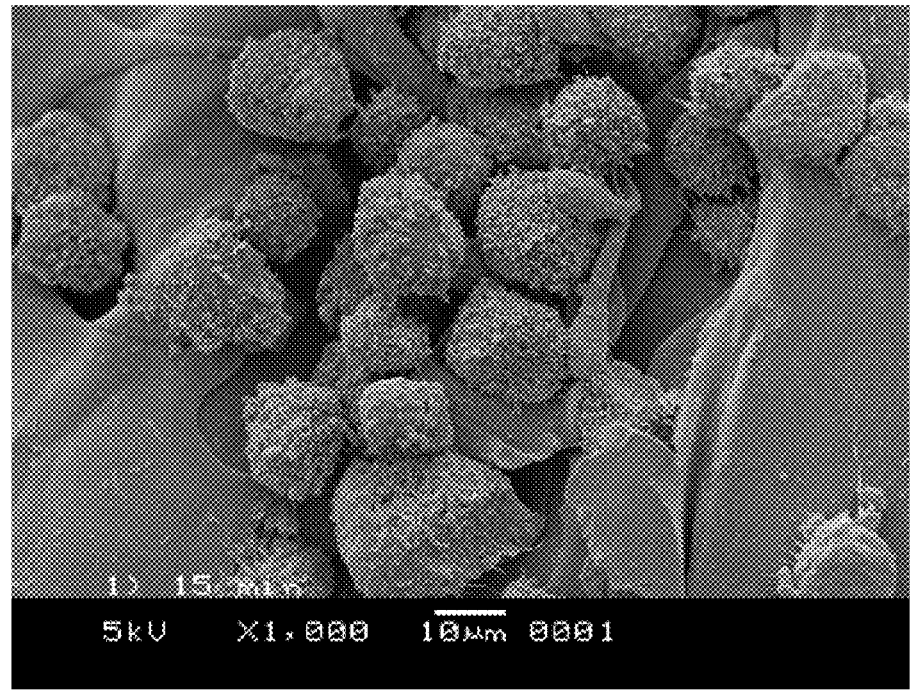
FIG. 16 is a SEM of a SFCS seeded with ADSC at 1000× magnification.

FIG. 11 is a scanning electron micrograph (SEM) of unseeded ADM at a magnification of 100×. As can be seen in FIG. 11, the ADM is characterized by a surface having three dimensional mounds and ridges at a periodicity of 10-100 µm. FIG. 12 is a SEM of the ADM seeded with ADSC. As can be seen in FIG. 12, the seeded cells spread out on the rough surface. FIG. 13 represents a 1,000× magnification of unseeded ADM, wherein it can be seen that the ADM not only presents a surface having three dimensional mounds and ridges at a periodicity of 10-100 µm but also presents surface irregularity on a scale of 1-10 µm. FIG. 14 represents the ADM at 1000× magnification now seeded with ADSC where it can be seen that the ADSC are spread out and adherent to the surface of the matrix.

Once on the operative field, grafts were transferred to a sterile 6-well plate and washed gently in 2×500 µl aliquots of PBS to remove any non-adherent cells or medium. For the main study groups of seven athymic nude mice were randomized to one of three treatment groups: no graft, ADM alone or ADSC-ADM. Animals in each group received one 6 mm punch lesion and a graft-based repair depending on group randomization.

Human adipose-derived stem cells have been well characterized with regard to profile of expressed surface cluster of differentiation (CD) markers. The ADSCs were negative for the pan-leukocyte marker CD45, separating them from the hematopoietic lineage. They were also negative for the integrin CD11b (alpha-M chain), an adhesion molecule characteristically found on macrophages and leukocytes. The ADSCs were positive for CD44 (99±1%), CD90 (98±3%), CD105 (98±2%).

Analysis of wound healing rates (rate of wound contraction) was defined as the gross epithelialization of the wound bed. A statistically significant increased rate of epithelialization in the ADSC-ADM group compared to the no-graft and ADM groups was noted at postoperative day 7. Percent wound closure at post-op day 7 was 56±21% in the no-graft control group, 57±21% in the ADM group and 77±4% in the ADSC-ADM group (p≤0.05). Closure of wounds in the ADSC-ADM group still was significantly greater than in the no-graft group at post-op day 10, although the differences between the three groups diminished over time as would be expected. Because the ADSC were transfected with a vector expressing Green Fluorescent protein (GFP) prior to seeding of the grafts, the status of the ADSC could be monitored during wound healing. It was found that the ADSC actively proliferated post transplantation and could be detected in the graft at 28 days, almost two weeks after complete wound closure. Certain of the ADSCs engrafted into the cutaneous wound milieu via the ADSC-ADM construct demonstrated a microvascular endothelial phenotype by 2 weeks postoperatively, contributing directly to the establishment of a vascular network in the context of tissue regeneration. No GFP expressing cells were detectable at locations 2 cm from the graft, nor in the spleen, liver or kidneys, indicating that the transplanted cells were locally persistent to the site of engraftment.

The findings demonstrated that a construct created by the seeding of adipose-derived stem cells upon human dermal matrix could be used as an effective delivery vehicle in vivo. Furthermore, the use of an ADSC-seeded ADM construct significantly enhanced the rate of wound healing at postoperative day 7. Finally, it was demonstrated that human adipose-derived mesenchymal stem cells delivered via an ADSC-ADM construct persist locally and do not distribute systemically, providing anatomically directed support to tissue regeneration at the desired site of surgical engraftment.

As an important finding of this study, it was shown that human adipose-derived stem cells delivered via dermal matrix differentiated into derivatives of two germ layers in the setting of this murine cutaneous wound healing model. Ectoderm derivatives were noted at 4 weeks at which time GFP positive stem cells were seen to co-localize with stain against cytokeratin 19, an element of epidermal epithelium, indicating differentiation into epidermal epithelial cells. Spontaneous mesoderm-derivative differentiation patterns were evidenced by GFP-positive ADSCs co-staining with HSP47, an indicator of a fibroblastic differentiation fate. Further evidence of mesodermal differentiation paths was observed with the identification of smooth muscle actin (SMA)-positive and von Willebrand Factor-positive engrafted GFP cells, appearing structurally integral to and associated with neo-vascular structures. This finding is consistent with the recent report by Wu and colleagues on the ability of $1 \times 10^6$ mesenchymal stem cells delivered to the cutaneous wound to differentiate into various dermal appendages. (Wu Y, et al. "Mesenchymal stem cells enhance wound healing through differentiation and angiogenesis" *Stem Cells* 25(10) (2007) 2648-59).

Consistent with the observed enhanced rate of wound healing, a circumferential halo of hyperemia was noted at the margins of the healing wounds in the ADSC-ADM group, observed most prominently at postoperative day 7, which was not seen in the no-graft or ADM groups. Kim and colleagues recently reported on markedly enhanced rates of gross wound closure in athymic mice treated locally with a dose of $1 \times 10^6$ ADSCs. (Kim W S, et al. "Wound healing effect of adipose-derived stem cells: a critical role of secretory factors on human dermal fibroblasts" *J Dermatol Sci* 48(1) (2007) 15-24). The present study indicates that with the use of a carrier system a therapeutic effect is facilitated with only a fifth of the cells ($2 \times 10^5$).

Silk-Chitosan Scaffolds:

In one embodiment of the invention, a particularly treated blend of silk fibroin and chitosan is provided that is pre-seeded with reparative cells prior to implantation. The fibers of silkworm silk consist of two main proteins, fibroin, which is the structural center of the silk fiber and sericin, which is the sticky material surrounding the fibroin. Silk fibroin is a β-keratin material known to be a reliable suture material with mid-range degradation kinetics and solid mechanical strength. Silk fibroin which has unique biocompatibility features including its degradation products. Silk fibroin degrades to amino acids, which are natural to the body.

Chitosan is a naturally occurring polysaccharide composed of alternating acetylated and deacetylated D-glucosamine residues. The polysaccharide is derived from the deacetylation of the exoskeleton of crustaceans and having the chemical formula Poly-(1-4)-2-Amino-2-deoxy-β-D-Glucan as reflected in the following structure:

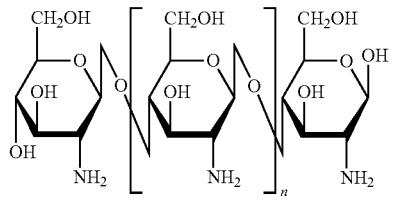

Chitosan has been used clinically in hemostatic wound dressings and is emerging as a promising constituent of novel biocompatible matrices in tissue engineering. (Khor E, Lim L Y. "Implantable applications of chitin and chitosan." *Biomaterials* 24(13) (2003) 2339-2349). Chitosan degrades to sugars, also part of the body's metabolism and easily incorporated into other metabolic products. Since the degradation of the product does not change the local pH, there is no adverse effect such as observed with polyglucolic or polylactic acids, whose degradation reduces the local pH and causes a sterile inflammatory response.

Silk fibroin combined with chitosan has been found to be useful in repair of tissue defects. See e.g. Gobin A S, Butler C E, and Mathur A B. "Repair and regeneration of the abdominal wall musculofascial defect using silk fibroin-chitosan blend." *Tissue Eng* 12(12) (2006) 3383-3394. Silk fibroin can be blended with chitosan at different ratios including 25:75, 50:50, 60:40, or 75:25, with the different ratios providing different physical characteristics.

Example 6

Silk fibroin-chitosan scaffolds were prepared in a series of steps. The sericin coating of raw silk fiber was removed via degumming. Solutions of 0.25% (w/v) sodium dodecyl sulfate (Sigma-Aldrich, St. Louis, Mo.) and 0.25% (w/v) sodium carbonate (Sigma-Aldrich) were dissolved and heated to 100° C. Silk was added at 1:100 w/v, heated for 1 hour, followed by draining of the alkaline soap solution. Degummed silk was rinsed in running distilled water, air-dried, and then dissolved in calcium nitrate tetrahydrate-methanol (molar ratio 1:4:2 calcium:water:methyl alcohol) at 65° C. The silk fibroin (SF) was dissolved at 10% (w/v) concentration over a 3-h period with continuous stirring.

Chitosan (CS) solution was prepared by 2% acetic acid dissolution of high-molecular-weight chitosan (82.7% deacetylation; Sigma-Aldrich). Under continuous stirring, SF and CS solutions were combined for preparation of 75:25 (v/v) SF:CS blend, followed by mixing for 30 minutes, and then dialysis (molecular weight cutoff, 6-8 kDa) for 4 days against deionized water.

Forty ml of SFCS blend solution was added to a glass Petri dish and then non-directionally frozen overnight at −80° C., followed by 2-day lyophilization. Dry samples were treated in a 50:50 (v/v) methanol:1N sodium hydroxide (NaOH) solution for 15 minutes for SF crystallization and CS neutralization. Methanol:NaOH was then replaced by 1 N NaOH for 12-18 hours. NaOH was removed by dilution in phosphate-buffered saline (PBS, 1×) with sequential changes of solution hourly for 4 hours and then quarter-hourly until pH equilibration at 7.0. Samples were sterilized with 70% ethanol immersion for 12-18 hours, and subsequently rinsed in sterile PBS prior to in vitro cell seeding and subsequent in vivo engraftment. Final scaffold thickness was 1.5 mm.

In other embodiments, thin sections of SFCS were fabricated using a 75:25 SFCS blend. One ml of a 75:25 SFCS blend was added to a flexiperm mold adhered to a glass slide and oven dried at ~60° C. overnight. The SFCS film was treated with 50:50 (v/v) methanol:1N NaOH for 15 minutes for SF crystallization and CS neutralization. The methanol: NaOH was replaced by 1 N NaOH for 12-18 hrs and the NaOH removed by dilution in PBS 2-3× for 30 minutes until the pH equilibrated at 7.0. Again the SFCS film was sterilized by 70% ethanol immersion for 12-18 hours. After rinsing with sterile PBS the SFCS scaffold was ready for seeding.

In an experiment to test the functionality of pre-seeded silk-fibroin grafts made as described above versus unseeded grafts, human ADSC-seeded SFCS were tested as a cytoprosthetic hybrid for reconstructive support in a murine cutaneous wound healing model. ADSC-SFCS were found to support the delivery and engraftment of stem cells as well as differentiation into fibrovascular and epithelial components. Human adipose tissue was obtained from elective body contouring procedures and the tissue digested with a solution of 0.07% Blendzyme 3 (F. Hoffman-La Roche Ltd, Basel, Switzerland) with mild agitation at 37° C. for 60 minutes, passed through a 40 µm filter and finally selected based on adherence to T75 tissue culture flasks at 24 hours. Cells were grown in alpha MEM medium supplemented with 20% fetal bovine serum, 2 mM L-glutamine, 100 U/ml penicillin, and 100 µg/ml streptomycin. Cells were incubated in a 5% $CO_2$-containing chamber at 37° C. with medium changed every 3 days. ADSCs between passages 1 and 8 were used for all experiments. ADSCs used in these experiments have been previously characterized and the multi-lineage differentiation potential of these cells demonstrated. (Bai X, et al. "Electrophysiological Properties of Human Adipose Tissue-Derived Stem Cells." *Am J Physiol Cell Physiol* 293(5) (2007) C1539-50).

For seeding of the grafts, six-mm diameter SFCS grafts were placed completely covering the well bottom in 96-well plates and the grafts were covered with 200 µl aliquots of medium alone in the SFCS group and with equal volume of cell suspension containing $1 \times 10^5$ ADSCs/cm$^2$ in the ADSC-SFCS group. Grafts were incubated under standard culture conditions for 24 hours after which overlying medium or cell suspension was aspirated. The grafts were flipped to place the opposite surface facing up, and the corresponding medium or cell suspension solution was placed on the other side. Grafts were then incubated for 24 hours and transferred to the operating suite for surgical engraftment. Once on the operative field, grafts were transferred to a sterile 6-well plate and washed gently in 2×500 µl aliquots of PBS to remove any non-adherent cells or medium. For the main study ten animals were randomized to one of three treatment groups: no graft, SFCS alone or ADSC-SFCS. Animals in each group received one 6 mm punch lesion and a graft-based repair depending on group randomization.

Wound closure was measured by planimetric analysis and revealed a wound closure at post-op day 6 of 46±15% in the control group receiving no graft, 58±9% in the SFCS group and 72±5% in the ADSC-SFCS group (p≤0.05). Post-op day 8 values were 55±17% in the no graft group, 75±11% in the SFCS group and 90±3% in the ADSC-SFCS group (p≤0.05). Wound bed analysis of fresh tissue mounts demonstrated a markedly enhanced extent of wound closure in the ADSC-SFCS group in comparison to both the SFCS and no-graft control groups at post-op day 9. Close inspection of images under intense illumination revealed an apparent more robust invasion of vascular tissue, characterized by hyperemia, in the SFCS and ADSC-SFCS groups versus no-graft controls. Furthermore, the extent of vascular infiltration of the surrounding tissue in the region of the operative site was greater in qualitative magnitude in the ADSC-SFCS group versus the SFCS group (data not shown). Mean micro-vessel density in the ADSC-SFCS group at 2 weeks post-op was 7.5±1.1 vessels/high power field, while density in the SFCS group at two weeks was 5.1±1.0 vessels/high power field (p≤0.05). There was no evident inflammatory infiltrate (no polymorphonuclear cell infiltration, no giant cells noted) on any H&E stains of wound bed biopsies at two weeks, indicating excellent biocompatibility of engrafted SFCS. FIGS. 13 *and* 14 are scanning electron micrographs of SFCS seeded with ADSC. As can be seen in the images, the ADSC preferentially adhere to regions having surface structure or micro-roughness.

This study showed that a 75:25 silk fibroin-chitosan blend acts as a scaffold for the seeding and in vivo delivery of human adipose-derived stem cells and confers the physiologic benefits of accelerated wound closure. Histological analysis showed that the ADSCs engraft, proliferate and differentiate into fibroblastic, vascular, and epithelial phenotypes in their new microenvironment and that such seeded grafts potentiate local vascular ingrowth. The culture-expanded ADSCs were shown to adhere to a SFCS substrate in the range of 75% adhesion by one hour post-seeding, with adherent stem cells occupying both surface and three-dimensional elements of the scaffold. The clear engraftment of ADSCs into regenerating tissue in this study differs from previous reports where the engraftment of therapeutically introduced mesenchymal stem cells has been either un-observable or observable only at low levels. (Prockop D J. "'Stemness' does not explain the repair of many tissues by mesenchymal stem/multipotent stromal cells (MSCs)" *Clin Pharmacol Ther.* 82(3) (2007) 241-243).

Successful seeding of grafts has been conducted with fresh SVF cells as well and provides the further benefits of larger numbers of cells loaded on the graft and a greater population diversity as well.

Seeding of the Matrices

Cells for regenerative medicine can be delivered as a suspension, including delivery of suspensions of cells to specific target compartments. For example, one of the present inventors has disclosed a process for repairing tissue by delivering stem cells to a site of the tissue to be repaired through the vascular tree or the pre-existing distribution trees in the body and that such focal application of cells is beneficial, for example for repair of a patient's heart, brain, liver, kidney, pancreas, lungs, nerves, and muscles. (Alt, E., U.S. Pat. No. 6,805,860 and related CIP Application issuing as U.S. Pat. No. 7,452,532).

While delivery of cell suspensions may be indicated in certain tissue repair or regeneration applications, in other indications it may be desirable to localize the cells in high concentration on a matrix or scaffold in order to provide a locally enriched population of desired cells and to retain their presence at the site of desired action until healing is well underway. Provided herein are methods and compositions that are able to seed and retain cells of interest on a biocompatible scaffold. Also provided are methods to most effectively use the scaffold in conjunction with a freshly isolated cellular preparation that avoids a need for culturing of the cells. In other embodiments, methods and compositions are provided to selectively enrich for cells that are desired in specific tissue regeneration applications based on their adherence to different biomaterials, while removing cells that may be detrimental to the tissue repair or regeneration process.

In one embodiment of the invention, the reparative cell population is isolated as above and immediately seeded onto a biocompatible matrix. In other embodiments, the stromal vascular fraction is isolated and subject to culture to isolate the adherent cells that have been characterized as mesenchymal stromal cells. The adherent cells are seeded onto scaffolds and, as further shown herein, will adhere to the scaffold within 2 hours and preferably within one hour.

In one embodiment of the invention, the reparative cell isolation apparatus such as that depicted in FIG. 6 includes an in-line seeding chamber 180. For example, as described in FIG. 7, the SVF fraction is removed from under the lipid containing layer in the lipid separating chamber 140 and the SVF cells are pulled or pushed into the seeding chamber 180 by the action of a pump (not shown) that can be place up or downstream of the seeding chamber. For example, where a porous scaffold is used, the cells can be forced into rapid contact with the surface of the scaffold when the fluid medium containing the cells is pulled through the scaffold. After a contact time whereby a desired % of the desired cells have adhered to the scaffold, nonadherent cells and debris are removed through nonadherent conduit 187. In other embodiments, the seeding chamber 180 is a separate apparatus or unit from the isolation apparatus 100.

Optionally, a porous cell retentive membrane having pore size between 0.2 and 5 μm, preferably between 1 and 3 μm is situated immediately beneath the porous cell scaffold. The cells are forced into rapid contact with the surface of the scaffold when the fluid medium containing the cells is pulled through the scaffold and retained in contact or close proximity to the porous cell scaffold by the porous cell retentive membrane. Media to enhance cell adherence of desired reparative cells to the membrane may be introduced at this time. Media may include, but not be limited to, cell culture media supplemented with the patient's own plasma or serum, carbohydrates such as carboxymethyl dextran or iron dextran, or cold insoluble globulin. After a contact time of 5 minutes to 2 hours, non-retained cells and debris are removed through conduit 187. Media or porous membrane composition that may further support cell survival following implantation in situ may also be incorporated for example inclusion of local oxygen delivery component (U.S. Pat. No. 7,160,553). In other embodiments, the seeding chamber 180 is a separate apparatus or unit from the isolation apparatus 100.

In one embodiment, the seeding chamber 180 is a disposable unit that is loaded with the scaffold 185 before the cell isolation begins. The shape and size of this scaffold is adaptable to its intended clinical use, including shape and dimension and two or three dimensional configuration.

Figure 7:
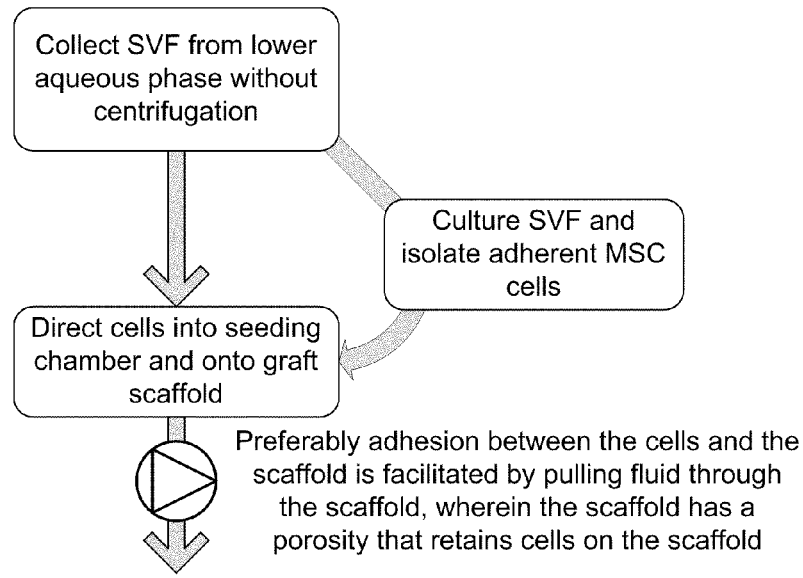
FIGS. 7 and 8 are flow charts depicting seeding methods according to two embodiments of the invention.

In one embodiment, as depicted in FIG. 7, procedural steps in use of a seeding chamber include the following: SVF or MSC are conveyed to a seeding chamber which is adapted for use depending on a configuration and cell selection criteria tailored to the tissue to be repaired. The cells are introduced into the seeding chamber in a way that promotes physical interaction between the cells and the matrix material of the scaffold and a certain contact time between 15 and 120 minutes is allowed for desired cells to attach and/or migrate into structure of the scaffold, following which cells that have not adhered to the scaffold are evacuated or washed from the seeding chamber.

Figure 8:
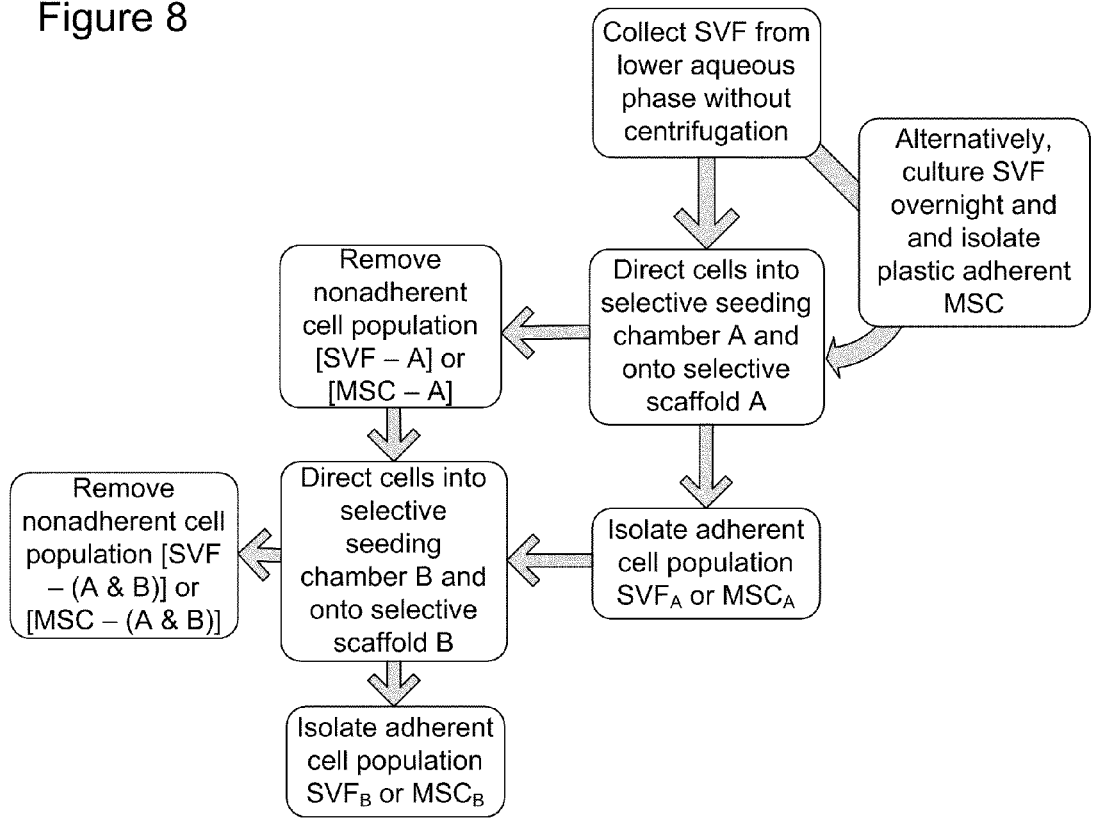

In one embodiment of the invention as depicted in FIG. 8, a series of selective seeding chambers are utilized in serial fashion. For example, SVF cells are isolated and directed into selective seeding chamber A wherein scaffold A is adapted to selectively bind a population of cells on the basis of an "A" ligand. Non-adherent cells lacking the "A" ligand are washed from the A chamber and directed to selective seeding chamber B, which contains selective scaffold B, which is adapted to selectively bind a population of cells on the basis of a "B" ligand. Non-adherent cells lacking both the "A" and "B" ligand are washed from chamber B and collected. Adherent cells in chambers A and/or B may be collected after release from the scaffolds. The selective seeding chambers may be used for either positive or negative selection in the generation of specific cell populations.

In one embodiment of the invention, introduction of the reparative cells onto the scaffold is facilitated by pulling the cells through a porous scaffold in such a way that physical contact between the cells and the surface of the scaffold is promoted. For example, the seeding can be enhanced by vacuum or other physical force applied to the cells to force the cells into physical contact with the matrix or scaffold. In one embodiment of a seeding chamber and method of use thereof, the cells are introduced to the chamber prior to an attachment period of less than 2 hours. For use, the scaffold is removed from the seeding chamber and applied to or implanted at the target site on a human or animal patient.

Figure 9A:
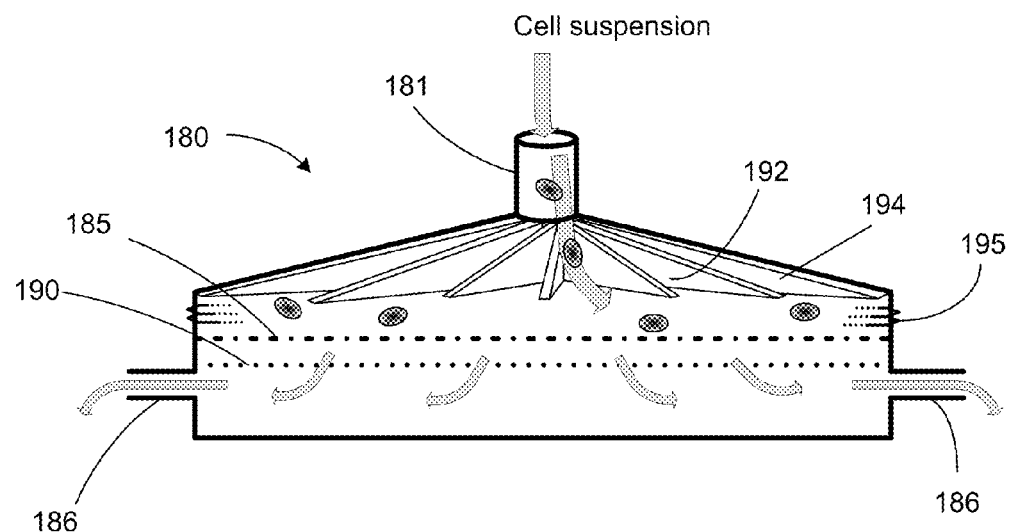
FIGS. 9A and B represent two alternative embodiments of cell seeding chambers.

FIG. 9A depicts one embodiment of a seeding chamber 180 wherein cells to be seeded onto scaffold 185 are introduced into seeding chamber 180 through inlet 181. In the depicted embodiment, scaffold 185 is mounted in the chamber in such a way that a fluid entering the chamber from inlet 181 may not leave through outlet 186 without passing through the scaffold 185. In the depicted embodiment, the scaffold 185 is supported by porous support 190. The chamber is designed so that no fluids can pass to outlet 186 without going through the scaffold 185. In this way, a pump or other partial vacuum source (not shown) disposed in fluid communication with outlet 186 is able to pull fluids through the scaffold and any cells entering the chamber will be rapidly pulled into contact with the scaffold. In the embodiment depicted in FIG. 9A, the top of the chamber includes a plurality of ribs 194 that are arrayed to convey fluid entering the chamber down channels 192 such that cells are relatively evenly dispersed over the scaffold surface. The top and bottom aspects of the chamber are connected by a resealable closure such as threaded closure 195, which enables ready opening of the chamber for insertion of the scaffold as well as removal of the cell seeded scaffold.

Figure 9B:
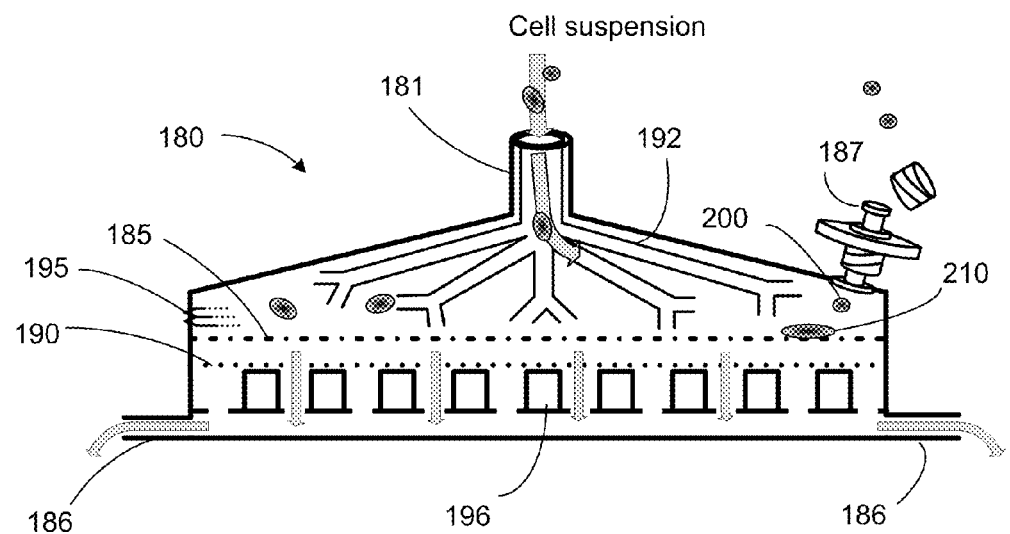

FIG. 9B depicts an alternative embodiment of a seeding chamber 180. Again cells to be seeded onto scaffold 185 are introduced into seeding chamber 180 through inlet 181. In the depicted embodiment, the upper portion of the chamber includes a port 187 whereby media can be exchanged, additive introduced, and cells that do not adhere to the scaffold can be drawn off after an incubation period. In the embodiment depicted in FIG. 9B, cells are relatively evenly distributed over the scaffold by a plurality of channels 192 that are manufactured into the lid or top of the chamber. Also in the depicted embodiment, the scaffold 185 is supported by a plurality of supports 196. Porous support 190 may not be necessary or desired. In one embodiment, the supports 196 represent the upper aspect of a grid or spiral or labyrinthine form having a plurality of drainage holes. The flow of fluid through the scaffold is essentially perpendicular to the plan of the scaffold as depicted by the arrows.

Figure 10:
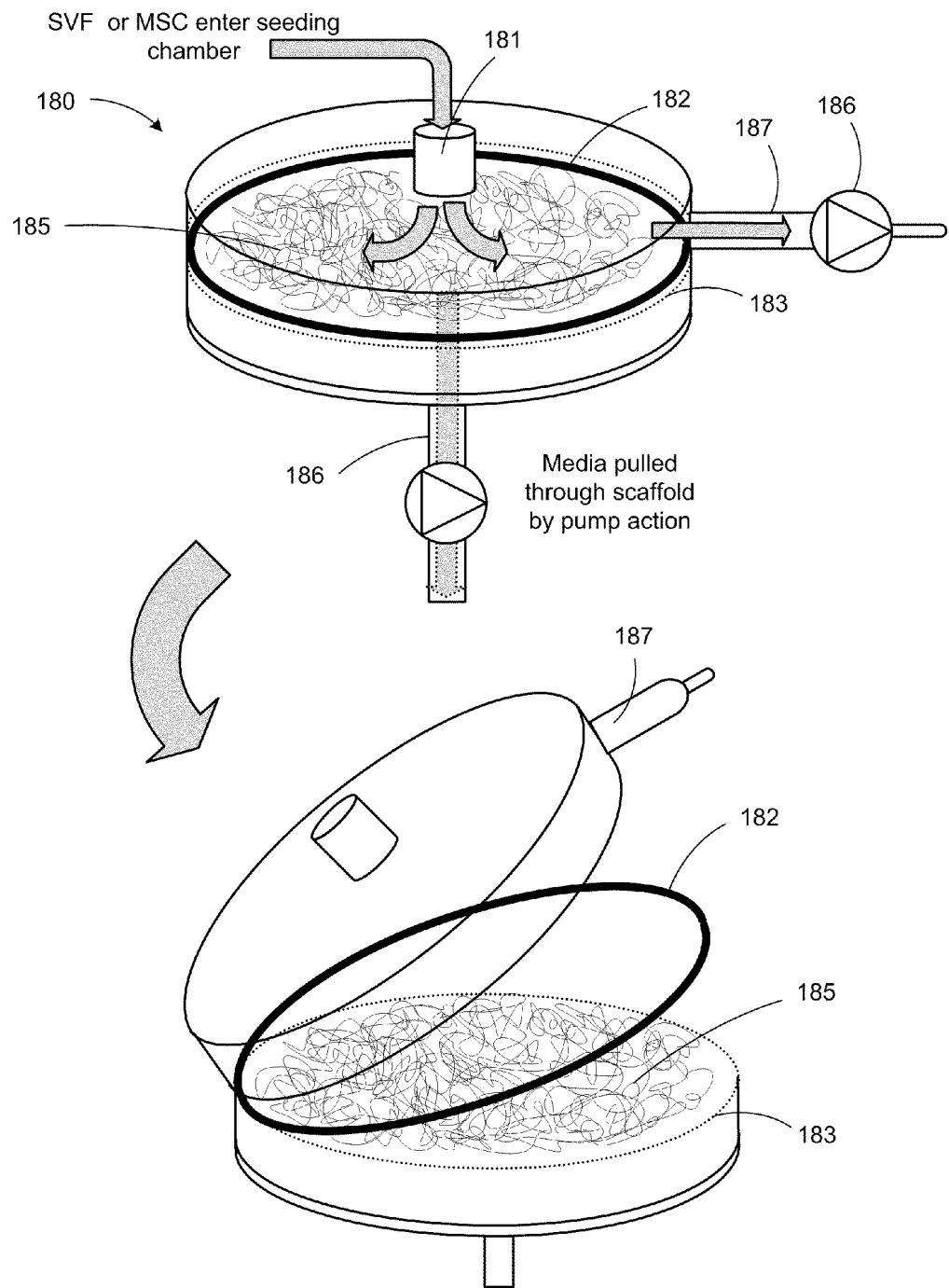
FIG. 10 depicts removal of a scaffold from a seeding chamber in accordance with one embodiment of the invention.

FIG. 10 depicts a seeding chamber according to one embodiment of the invention. Cells to be seeded onto porous scaffold 185 are introduced into seeding chamber 180 through inlet 181. In the depicted embodiment, porous scaffold 185 is mounted in the chamber in such a way that a fluid entering the chamber from inlet 181 may not leave through outlet 186 without passing through the scaffold 185. In one embodiment, a sealing ring 182 insures that no fluids can pass to outlet 186 without going through the scaffold 185. In this way, a pump or other partial vacuum source (not shown) disposed in fluid communication with outlet 186 is able to pull fluids through the scaffold and any cells entering the chamber will be rapidly pulled into contact with the scaffold.

After a predetermined attachment period, wash outlet 187 is opened and non-adherent cells and debris are pulled out of the chamber. If desired, a selective red blood cell lysis can be undertaken in the chamber, using for example hypotonic solutions, surfactants, ammonium chloride (155 mM $NH_4Cl$, 10 mM $KHCO_3$), carbamates (U.S. Pat. No. 7,300,797) etc., without compromising the viability of the nucleated cells.

Typically, as depicted in FIG. 10 the chamber 180 is constructed such that it can be opened after cells have been deposited on the scaffold and the scaffold removed for implantation or further processing.

Example 7

In one embodiment of the invention, the reparative cell population is contacted with the scaffold for less than about 90 minutes while in other embodiments, a contact time of approximately 60 minutes or even less is sufficient. A relatively short contact time was found to be effective in inducing the adherence of greater than 90% of adipose derived stem cells to a bioabsorbable ADM matrix. ADSCs were isolated from discarded adipose tissue obtained at body contouring procedures according to standard methodology for isolating mesenchymal stromal cells. Briefly, lipoaspirate was washed with sterile phosphate-buffered saline (PBS). Washed aspirates were treated with a mixture of collagenase and neutral protease in PBS for 30 min at 37° C. with agitation. The enzyme was inactivated with an equal volume of DMEM/10% fetal bovine serum (FBS) and the cells were collected by centrifugation for 10 min at low speed. The cellular pellet was resuspended in DMEM/10% FBS and filtered through a 100 μm mesh filter to remove debris. The filtrate was centrifuged as before and plated onto conventional tissue culture plates DMEM/20% FBS for culture. Non-adherent cells were removed after 24 hours by aspiration and the adherent cells were expanded in culture with media changes at 3 day intervals. Cells at passage 1-8 were used for experiments.

ADM of thickness 0.4 to 0.8 mm was obtained (AlloDerm®, LifeCell, Branchburg, N.J. and FlexHD™, MTF, Edison, N.J.). Passage 1-5 cell suspensions in growth medium were seeded into multi-well plates covered with ADM with the papillary dermis side facing up at a density of $5.0 \times 10^4$ cells/cm$^2$ for histology, $7.5 \times 10^4$ cells/cm$^2$ for quantitative studies, and $1.0 \times 10^6$ cells/cm$^2$ for scanning electron microscopy (SEM).

Adherence was quantified by fluorescent cell counts at 15, 30, 60 and 120 minutes. Specimens for histology and SEM were seeded and incubated under standard culture conditions for 24 hours. Specimens were hematoxylin and eosin (H&E) stained. SEM was performed using adaptations of established methodology.

The ADSCs were negative for the leukocyte markers CD45 and CD11b, and positive for the intermediate filament nestin, CD44, CD90, and CD105. Quantitative adhesion experiments revealed very rapid adherence of ASC to the ADM. It was found that 543±62 cells/mm$^2$ adhered at 15 minutes (71%), 688±69 cells/mm$^2$ adhered at 30 minutes (92%), 713±63 cells/mm$^2$ adhered at 60 minutes (94%), and 727±54 cells/mm$^2$ adhered at 120 minutes (96%). H&E and SEM analysis confirmed stem cell adhesion to ADM.

This experiment showed that the AdSC components of the reparative cell mixture are able to rapidly bind to a bioabsorbable ADM matrix. Thus, the ADSC present in the reparative cell mixture can be seeded onto a matrix and be available for implantation in one operative procedure. The observation that ADSCs adhere to ADM at high rates within a two-hour time frame is significant. Furthermore, SEM identified active attachment of stem cells to ADM with the extension of microvilli and lamellopodia acting as focal anchorage points.

Example 8

The rapid seeding of SFCS scaffolds was also tested to confirm the feasibility of point of care seeding of scaffolds. ADSC were isolated as described in Example 5 and seeded onto SFCS scaffolds produced as described in Example 4. For adhesion studies, cells were transfected with green fluorescent protein as described by Zhang et al. "Transduction of bone-marrow derived mesenchymal stem cells by using lentivirus vectors pseudotypes with modified RD114 envelope glycoprotains" *J. Virol.* 78 (2004) 1219-29. Adherence was qualtified by direct triplicate counts of adherent GFP positive cells.

It was shown that 75% of a population of ADSC would bind to a SFCS scaffold within 60 minutes. Specifically, in one experiment the numbers of adherent ADSCs to SFCS with time were as follows:

369±53.16 adherent cells/field (49.20±7.09% of seeded cells) at 15 minutes

365±81.30 adherent cells/field (48.78±10.84% of seeded cells) at 30 minutes

566±75.05 adherent cells/field (75.46±10.01% of seeded cells) at 60 minutes

572±131.33 adherent cells/field (76.30±17.51% of seeded cells) at 120 minutes

Figure 17:
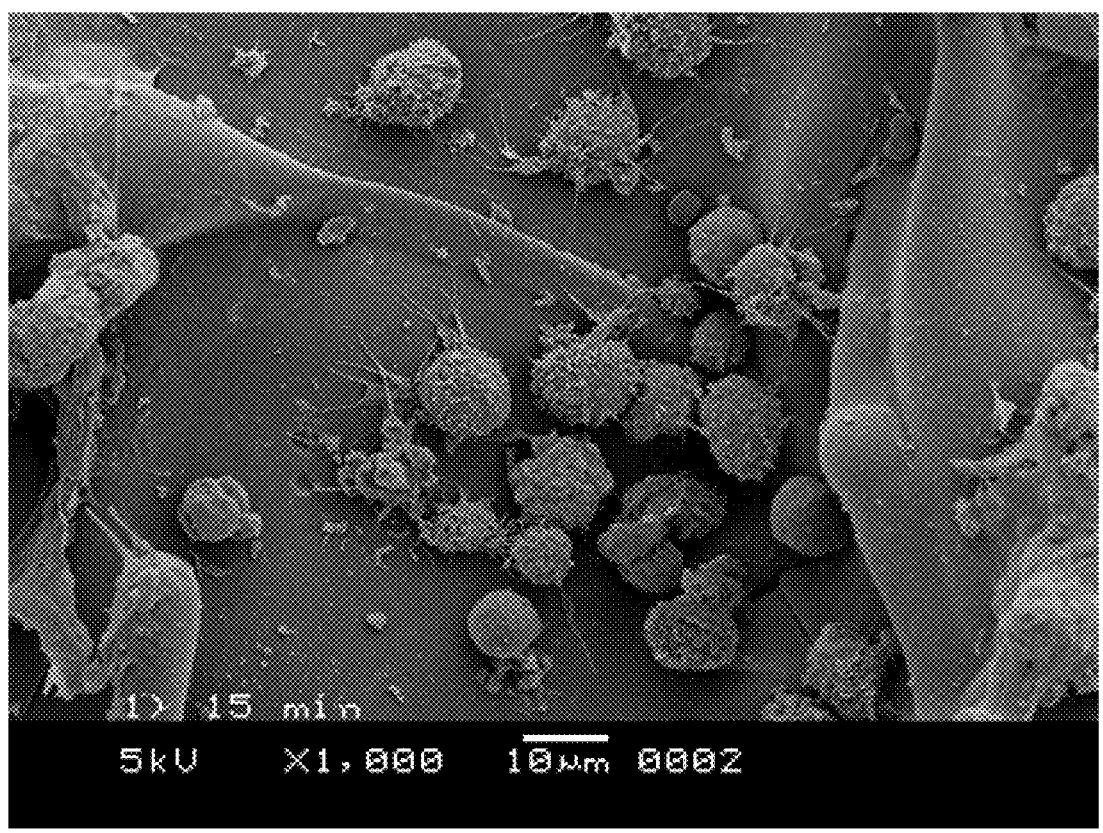
FIG. 17 is a SEM of a SFCS seeded with freshly isolated SVF cells at 1000× magnification.

SEM findings provided qualitative confirmation of the above adhesion data that was based on GFP fluorescent counts. A scatter distribution of adherent stem cells was observed at 15 minutes post-seeding, with adherent cells focused on the parallel sheet edge and around fiber projections of the surface. Cell spreading was noted by 30 minutes and by 60 minutes cells were beginning to adhere to the flat and smooth regions of the SFCS sheet that were initially minimally populated. By 120 minutes a full blanketing was observed with progressive spreading of cells on flat regions and the dense occupation of fiber convolutions and microenclaves at the junctions of fibers and sheets. The results obtained with ADC isolated with a step including plastic adherence were confirmed with freshly isolated cells. FIG. 17 presents a SEM image of freshly isolated SVF cells adhering to SFCS after 15 minutes of incubation. As can be seen, many of the cells have elaborated microvilli and lamellopodia by such time.

The results showed a preference of the cells for adherence to rough topography and pointed to this preferential structural character of particularly desirable scaffolds. Thus, in one embodiment of the invention a method of inducing adherence of reparative cell populations to tissue scaffolds includes generation of a rough surface topography to the scaffold wherein the surface is characterized by surface irregularities occurring on a scale of one to one hundred μm.

Preorientation of ADC and SVF:

In one embodiment of the invention, adherent cells from human lipoaspirate isolated in accordance with Example 1 and 2 are exposed to select induction media to preorient responsive cells into a desired differentiation track prior to administration into the patient. The following are non-limiting examples of induction media that are known to drive the differentiation of cells into particular lineages by prolonged culture in the media.

| Examples of Media for Cell Pre-orientation | | |
| --- | --- | --- |
| Lineage | Component | Conc. |
| Adipogenic | DMEM, low glucose | |
| | Fetal bovine serum (FBS) | 10% |
| | L-glutamine | 2 mM |
| | Penicillin/Streptomycin | |
| | L-Ascorbic acid | 100 µM |
| | 1-methyl-3-isobutylxanthine, (IBMX) | 0.5 mM |
| | Dexamethasone | 1 µM |
| | Indomethacin | 100 µM |
| | Insulin human recombinant | 10 µg/ml |
| Assess subsequent adipogenesis by Oil Red O staining | | |
| Chondrogenic | DMEM, high glucose | |
| | FBS | 10% |
| | Dexamethasone | 0.1 µM |
| | Ascorbate-2-phosphate | 25 ug/ml |
| | Insulin, bovine | 10 µg/ml |
| | TGFβ-3 (R&D) | 10 µg/ml |
| | Sodium pyruvate | 1 mM |
| | Non-essential amino acids | |
| | Proline | 0.M |
| | Transferrin | 5.5 µg/ml |
| | Sodium selenite | 5 ng/ml |
| | Linoleic Acid | 4.7 ng/ml |
| | Bovine Serum Albumen (BSA) | 0.5 mg/ml |
| Assess chondrogeneis by expression of proteoglycan or collagen II using histochemistry or immunohistochemistry staining. | | |
| Endothelial | DMEM, (low glucose) | |
| | FBS | 2% |
| | Penicillin | 10 U/ml |
| | Streptomycin | 100 ug/ml |
| | VEGF | 50 ng/ml |
| | L-glutamine | 2 mM |
| Assess endothelial like cells by detection of vWF by immunohistochemistry. | | |
| Hepatogeneic | DMEM, (1 g/L glucose) | |
| | FBS | 1% |
| | bFGF (Chemicon) | 10 ng/ml |
| | aFGF (Chemicon) | 20 ng/ml |
| | EGF | 10 ng/ml |
| | HGF (R&D) | 20 ng/ml |
| | Insulin-transferrin-selenious acid (ITS-BD Biosciences) | 1% |
| | Oncostatin M (OSM) | 10 ng/ml |
| Assess hepatogenesis by detection of albumin by immunofluorescence. | | |
| Myogenic | DMEM, (low glucose) | |
| | FBS | 10% |
| | Horse Serum (HS) | 5% |
| | Penicillin/streptomycin | 1% |
| | Hydrocortisone | 50 µM |
| Assess myogenesis by detection of myosin by immunofluorescence. | | |
| Neurogenic | DMEM, F12 | |
| | FBS | 1% |
| | B27 (Invitrogen) | 2% |
| | L-ascorbic acid | 50 µM |
| | Insulin | 5 µg/ml |
| | bFGF (Chemicon) | 10 ng/ml |
| | bEGF | 10 ng/ml |
| | NGF (R&D) | 10 ng/ml |
| | 2-mercaptoethanol | 1 mM |
| | forskolin | 10 µM |
| | cAMP | 2 mM |
| | 1-methyl-3-isobutylxanthine, (IBMX) | 0.5 mM |
| | indomethacin | 200 µM |
| Assess neurogenesis by detection of microtubule-associated protein-2 (MAP-2) by immunofluorescence. | | |
| Osteogenic | FBS | 10% |
| | Dexamethasone | 0.1 µM |
| | L-Ascorbic acid | 0.2 mM |
| | β-glycerol phosphate | 10 mM |
| Assess subsequent mineralization by calcium deposit by staining with Alizarin Rd S | | |

Applications

The cellular preparations of the present invention including the different biocapatable matrices can be applied to subjects for various cell therapeutic purposes. Such cell therapies generally refer to the regeneration and/or repair of injured or diseased tissue. Non-limiting examples include wound healing (infected and non-infected), bone fracture healing, treatment of non-healing ulcers, hernia repair, tendon repair, plastic surgical indications including skin grafting, cartilage regeneration, including cartilage of the nose and pinna of the ear, engraftment after chemotherapy, rescue of retinal degeneration, treatment of ischemic disease (e.g., ischemic heart disease and peripheral arterial disease), treatment of nerve injury, filling of heart aneurysms and of the atrial appendage, creation of an artificial bladder and bladder wall repair, repair and reconstruction of intestines, and repair and reconstruction of vessels and associated structures.

Cardiac Applications: In one embodiment, reparative populations are seeded onto biomaterial matrices for the treatment of various physical defects of the heart including the roughly 1% of the population with an atrial septal defect which enables a shunt between the right and left atrium. Other deficiencies are ventricular septum defect and patent foramen ovale (PFO) that are amenable by occlusion either by direct surgical techniques in suturing a cell seeded patch or by non-invasive correction in placing a cell seeded occluder. While all current occluders and materials to close such a patch are considered to be of non-absorbable materials such as Teflon®, Dacron®, stainless steel, Elgiloy® or Nitinol™, the present invention provides biomaterials which are absorbable and coated with stem cells which allows a natural healing as certain of the included multipotent cells differentiate into fibroblasts as well as cardiomyocytes.

Another application for the biomaterial is to occlude the left auricle of the left atrium from which a good deal of thrombotic events can occur and previous experience has shown that the occlusion of such an auricle can reduce the formation of thrombus and prevent the embolic events. In another embodiment, reparative cell coated biomaterial is used for repair of aneurysms of the vascular structures, including aneurysms of the aorta and arteries. Placement can optionally be made from inside the vessel in the form of a covered stent, which would be a combination of a scaffold and a coated biomaterial membrane.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. A method of generating a cell-seeded tissue graft comprising:
isolating stromal vascular fraction (SVF) cells from an adipose tissue of a mammal to produce a fresh cellular preparation, said SVF cells isolated by a process including enzymatically digesting adipose tissue;
applying the SVF cells to a porous scaffold,
wherein the SVF cells have not been subjected to plastic adherence;
applying the unbound cells to a second scaffold, wherein the second scaffold is adapted for binding of a different subpopulation of cells than the first scaffold,
thereby generating a cell-seeded tissue graft from the first and/or the second scaffold.

2. The method of claim 1, wherein the first and/or the second scaffold is characterized by a micro-rough cell attachment surface that has surface irregularities at a periodicity of 1-20 μm.

3. The method of claim 1, wherein the SVF cells are collected without centrifugation.

4. The method of claim 1, wherein the cell-seeded tissue graft is generated at a point-of-care and is implanted into the mammal without culturing the cell-seeded tissue graft.

5. The method of claim 1, wherein the cell-seeded tissue graft is cultured to expand populations of cells seeded on the graft prior to implanting into the mammal.

6. The method of claim 1, wherein the SVF cells are pushed into contact with the first and/or second scaffold by pressure.

7. The method of claim 1, wherein the SVF cells are pushed into contact with the first and/or second scaffold by a partial vacuum.

8. The method of claim 1, wherein the SVF cells are incubated with inductive media before, during or after being applied to the first and/or second scaffold.

9. The method of claim 8, wherein the inductive media is adapted for generation of one or more of adipocytes, chondrocytes, endothelial cells, hepatocytes, myoblasts, neurons, and osteoblasts.

10. The method of claim 1, wherein the first and/or second scaffold is comprised of a biocompatible or a biodegradable material.

11. The method of claim 10, wherein the biocompatible material is selected from the group consisting of: polytetrafluoroethylene, woven polyester, spun silicone, open foam silicone encased in microporous expanded PTFE, stainless steel, polypropylene, polyurethane, polycarbonate, nickel titanium shape memory alloys and cobalt-chromium-nickel alloys, and combinations thereof.

12. The method of claim 10, wherein the biodegradable material is selected from the group consisting of: silk fibroin-chitosan, acellular dermal matrices, collagen, polyglactin, hyaluronic acid, and resorbable silica gel matrix.

13. The method of claim 2, wherein the surface irregularities are independent of a porosity of the first and/or second porous scaffold.

14. The method of claim 1, wherein the first and/or second scaffold is characterized by a micro-rough cell attachment surface that has surface irregularities at a periodicity of 1-10 μm.

15. The method of claim 2, wherein the surface irregularities of the first and/or second scaffold are created by treatment of at least one cell attachment surface of the scaffold by one or more of embossing, blasting, plasma etching, by controlling polymerization or drying processes, by heat application, by chemical etching, and by coating or printing.

16. The method of claim 10, wherein at least one surface of the first and/or second scaffold is characterized by a spongy texture formed by subjecting the nascent scaffold material to a partial vacuum during polymerization or drying.

17. The method of claim 1, wherein the cell-seeded tissue graft is utilized to treat one or more of: wound healing, burns, bone fractures, cosmetic defects, cartilage damage, tendon damage, ulcers, fistulas, hernias, retinal degeneration, treatment of ischemic disease, nerve injury, aneurysms, bladder wall repair, intestinal injury, and vascular vessel repair.

18. The method of claim 1, further comprising introducing one or more adherence agents into a seeding chamber that holds the scaffolds before or during cell seeding, said adherence agents selected to promote adherence of desired cell types to the first and/or second scaffold.

19. The method of claim 18, wherein the adherence agent is selected from the group consisting of: autologous plasma or serum and components thereof, cold insoluble globulin, carboxymethyl dextran, iron dextran, and hyaluronic acid and polymers thereof.

20. A method of seeding a plurality of cell scaffolds in seriatim comprising:
applying a mixed stromal vascular fraction (SVF) cell population that has been freshly isolated without plastic adherence to a first porous biodegradable scaffold in a first seeding chamber by flowing the mixed SVF cell population through the first porous biodegradable scaffold in a single passage through the first porous biodegradable scaffold;
conveying the unbound cells from the first porous biodegradable scaffold to a second porous biodegradable scaffold in a second seeding chamber and flowing the unbound cell population through the second porous biodegradable scaffold in a single passage through the second porous biodegradable scaffold,
wherein the second porous biodegradable scaffold is adapted for adherence of a different subpopulation of cells than the first porous biodegradable scaffold;
removing the unbound cells from the second seeding chamber; and
removing the first and second porous, biodegradable scaffolds, thereby generating at least two tissue grafts, each seeded with a different subpopulation of cells.

21. A method of generating a cell-seeded tissue graft comprising:
isolating a stromal vascular fraction (SVF) cell population from an adipose tissue of a mammal by a process including enzymatic digestion of the adipose tissue;
applying the SVF cell population to a first filter, wherein the SVF cell population has not been subjected to plastic adherence;
removing unbound SVF cell population from the first filter; and
applying the unbound SVF cell population to a second filter, wherein the second filter is adapted to bind a different subpopulation of cells from the SVF cell population than the first filter, thereby generating at least one cell seeded tissue graft comprising cells bound on the first and/or second filter.

22. The method of generating a cell-seeded tissue graft of claim 21, wherein the application of the SVF cell populations to the first and second filters provide positive and/or negative selection of cell populations.

23. A method of generating a cell-seeded tissue graft comprising:
isolating stromal vascular fraction (SVF) cells from an adipose tissue of a mammal to produce a fresh cellular preparation by a process including enzymatic digestion of the adipose tissue;
applying the SVF cells to a first matrix, wherein the SVF cells have not been subjected to plastic adherence;
removing unbound SVF cells from the first matrix; and
applying the unbound SVF cells to a second matrix, wherein the second matrix is adapted for binding of a different subpopulation of cells than the first matrix, thereby generating a cell seeded tissue graft.

24. A method of generating a cell-seeded tissue graft comprising:
isolating stromal vascular fraction (SVF) cells from an adipose tissue of a mammal, said SVF cells isolated by enzymatically digesting adipose tissue;

applying the SVF cells to a first filter, wherein the SVF cells have not been subjected to plastic adherence;

applying the SVF cells to a second filter, wherein the second filter is adapted for binding of a different subpopulation of cells than the first filter, thereby enabling positive and negative selection of cells.

* * * * *